United States Patent
Altshuler et al.

(10) Patent No.: US 11,224,336 B2
(45) Date of Patent: Jan. 18, 2022

(54) ROTATIONAL EXTENDER AND/OR REPEATER FOR ROTATING FIBER BASED OPTICAL IMAGING SYSTEMS, AND METHODS AND STORAGE MEDIUMS FOR USE THEREWITH

(71) Applicant: CANON U.S.A., INC., Melville, NY (US)

(72) Inventors: Alexander Altshuler, Cambridge, MA (US); Badr Elmaanaoui, Belmont, MA (US); Seiji Takeuchi, Newton, MA (US)

(73) Assignee: Canon U.S.A., Inc., Melville, NY (US)

( * ) Notice: Subject to any disclaimer, the term of this patent is extended or adjusted under 35 U.S.C. 154(b) by 429 days.

(21) Appl. No.: 16/184,832

(22) Filed: Nov. 8, 2018

(65) Prior Publication Data
US 2019/0150720 A1    May 23, 2019

Related U.S. Application Data

(60) Provisional application No. 62/587,805, filed on Nov. 17, 2017.

(51) Int. Cl.
*A61B 1/07* (2006.01)
*G02B 6/42* (2006.01)
(Continued)

(52) U.S. Cl.
CPC ............ *A61B 1/07* (2013.01); *A61B 1/00009* (2013.01); *A61B 1/00045* (2013.01);
(Continued)

(58) Field of Classification Search
CPC ..... A61B 8/12; A61B 1/00009; A61B 5/0084; A61B 1/07; A61B 5/0066; A61B 1/00126;
(Continued)

(56) References Cited

U.S. PATENT DOCUMENTS

| | | |
|---|---|---|
| 4,822,127 A | 4/1989 | Kamiya et al. |
| 6,010,449 A | 1/2000 | Selmon et al. |

(Continued)

FOREIGN PATENT DOCUMENTS

| | | |
|---|---|---|
| CN | 105193379 A | 12/2015 |
| EP | 2322912 A1 | 5/2011 |

(Continued)

OTHER PUBLICATIONS

Atif ["Catheters for optical coherence tomography", 2011 Laser Phys. Lett. 8 629] (Year: 2011).*

(Continued)

*Primary Examiner* — Oommen Jacob
(74) *Attorney, Agent, or Firm* — Canon U.S.A., Inc. I.P. Division

(57) ABSTRACT

One or more devices, systems, methods and storage mediums for characterizing, examining and/or diagnosing, and/or measuring viscosity of, a sample or object are provided herein. Such information may be obtained in application(s) using a system that includes a rotary junction, an elongated extender or at least one repeater attached to the rotary junction and a rotatable probe attached to the elongated extender and/or the at least one repeater. Examples of such applications include imaging, evaluating and diagnosing biological objects, such as, but not limited to, for Gastrointestinal, cardio and/or ophthalmic applications, and being obtained via one or more optical instruments. The extenders and/or repeaters may be used with one or more forms of imaging, such as, but not limited to, Spectrally Encoded Endoscopy ("SEE") and Optical Coherence Tomography ("OCT").

25 Claims, 19 Drawing Sheets

(51) Int. Cl.
| | |
|---|---|
| *H04N 5/225* | (2006.01) |
| *A61B 5/00* | (2006.01) |
| *A61B 1/00* | (2006.01) |
| *A61B 1/06* | (2006.01) |
| *A61B 8/12* | (2006.01) |
| *A61B 1/04* | (2006.01) |
| *A61B 3/12* | (2006.01) |
| *A61B 8/00* | (2006.01) |

(52) U.S. Cl.
CPC .......... *A61B 1/00126* (2013.01); *A61B 1/063* (2013.01); *A61B 5/0066* (2013.01); *A61B 5/0075* (2013.01); *A61B 5/0084* (2013.01); *A61B 5/7203* (2013.01); *A61B 8/12* (2013.01); *G02B 6/4206* (2013.01); *H04N 5/2254* (2013.01); *A61B 1/04* (2013.01); *A61B 3/1225* (2013.01); *A61B 8/4461* (2013.01); *A61B 2560/0443* (2013.01); *H04N 2005/2255* (2013.01)

(58) Field of Classification Search
CPC . A61B 5/7203; A61B 1/00045; A61B 5/0075; A61B 1/063; A61B 3/1225; A61B 2560/0443; A61B 1/04; A61B 1/00–07; A61B 8/4444–4466; A61B 5/6852; A61B 5/00; A61B 5/0062; H04N 5/2254; H04N 2005/2255; G02B 6/4206; G02B 23/2407; G02B 6/4246; G02B 23/2453; G01B 9/02091; G01B 9/0205; A61M 25/00
See application file for complete search history.

(56) References Cited

U.S. PATENT DOCUMENTS

| | | | |
|---|---|---|---|
| 6,341,036 B1 | 1/2002 | Tearney et al. | |
| 6,419,644 B1* | 7/2002 | White | A61B 8/12 600/466 |
| 6,450,964 B1* | 9/2002 | Webler | A61B 8/12 600/467 |
| 6,687,010 B1* | 2/2004 | Horii | G01B 9/0201 356/479 |
| 6,763,261 B2 | 7/2004 | Casscells, III et al. | |
| 7,366,376 B2 | 4/2008 | Shishkov et al. | |
| 7,382,949 B2 | 6/2008 | Bouma et al. | |
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,843,572 B2* | 11/2010 | Tearney | G01N 21/6458 356/479 |
| 7,859,679 B2 | 12/2010 | Bouma et al. | |
| 7,872,759 B2 | 1/2011 | Tearney et al. | |
| 7,889,348 B2 | 2/2011 | Tearney et al. | |
| 7,924,428 B2 | 4/2011 | Toida | |
| 8,045,177 B2 | 10/2011 | Tearney et al. | |
| 8,145,018 B2 | 3/2012 | Shishkov et al. | |
| 8,174,701 B2 | 5/2012 | Masuda | |
| 8,289,522 B2 | 10/2012 | Tearney et al. | |
| 8,676,013 B2 | 3/2014 | Bouma et al. | |
| 8,838,213 B2 | 9/2014 | Tearney et al. | |
| 8,928,889 B2 | 1/2015 | Tearney et al. | |
| 9,087,368 B2 | 7/2015 | Tearney et al. | |
| 9,254,089 B2 | 2/2016 | Tearney et al. | |
| 9,295,391 B1* | 3/2016 | Tearney | A61B 5/0059 |
| 9,332,942 B2 | 5/2016 | Jaffer et al. | |
| 9,351,705 B2* | 5/2016 | Wang | A61B 5/0068 |
| 9,360,630 B2 | 6/2016 | Jenner et al. | |
| 9,415,550 B2 | 8/2016 | Tearney et al. | |
| 9,557,154 B2 | 1/2017 | Tearney et al. | |
| 9,610,064 B2 | 4/2017 | Adler et al. | |
| 10,809,538 B2* | 10/2020 | Koyama | G02B 27/1013 |
| 2002/0183622 A1* | 12/2002 | Zuluaga | A61B 5/0084 600/476 |
| 2004/0017961 A1* | 1/2004 | Petersen | G01B 9/02091 385/12 |
| 2004/0111032 A1* | 6/2004 | Korn | A61B 5/0084 600/478 |
| 2007/0161893 A1* | 7/2007 | Milner | A61B 8/12 600/425 |
| 2007/0233396 A1* | 10/2007 | Tearney | G01N 21/4795 702/19 |
| 2007/0239032 A1* | 10/2007 | Milner | A61B 5/6852 600/476 |
| 2008/0177183 A1* | 7/2008 | Courtney | A61B 1/00172 600/463 |
| 2009/0018393 A1* | 1/2009 | Dick | A61B 5/0066 600/109 |
| 2009/0156941 A1 | 6/2009 | Moore | |
| 2010/0092389 A1 | 4/2010 | Jaffer | |
| 2010/0249601 A1* | 9/2010 | Courtney | A61B 5/6852 600/463 |
| 2011/0021926 A1* | 1/2011 | Spencer | A61B 5/0062 600/478 |
| 2011/0292400 A1 | 12/2011 | Fleming et al. | |
| 2012/0101374 A1 | 4/2012 | Tearney et al. | |
| 2013/0079644 A1 | 3/2013 | Peeters Weem et al. | |
| 2014/0276011 A1 | 9/2014 | Schmitt et al. | |
| 2016/0228097 A1* | 8/2016 | Jaffer | A61B 8/5269 |
| 2016/0287080 A1 | 10/2016 | Olesen et al. | |
| 2016/0349417 A1 | 12/2016 | Tearney et al. | |
| 2017/0035281 A1 | 2/2017 | Takeuchi et al. | |
| 2017/0135584 A1* | 5/2017 | Tearney | A61B 5/6852 |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0209049 A1 | 7/2017 | Wang et al. | |
| 2017/0290492 A1 | 10/2017 | Hamm et al. | |
| 2017/0322079 A1 | 11/2017 | Do et al. | |
| 2018/0017778 A1 | 1/2018 | Ikuta et al. | |
| 2019/0150720 A1* | 5/2019 | Altshuler | A61B 8/12 |

FOREIGN PATENT DOCUMENTS

| | | |
|---|---|---|
| JP | 2000-139925 A | 5/2000 |
| JP | 2013-540560 A | 11/2013 |
| WO | 2015/022760 A1 | 2/2015 |
| WO | 2015/116939 A1 | 8/2015 |
| WO | 2015/116951 A2 | 8/2015 |
| WO | 2016/015052 A1 | 1/2016 |
| WO | 2016/144878 A1 | 9/2016 |
| WO | 2017/024145 A1 | 2/2017 |
| WO | 2017/117203 A1 | 7/2017 |
| WO | 2017/165511 A1 | 9/2017 |

OTHER PUBLICATIONS

Atif, M., et al., "Catheters for optical coherence tomography", Laser Physics Letters, vol. 8, No. 9, Jul. 2011, XP055049797, ISSN: 1612-2011, DOI: 10.1002/lapl.201110035, pp. 629-646.

* cited by examiner

ROTATIONAL EXTENDER AND/OR REPEATER FOR ROTATING FIBER BASED OPTICAL IMAGING SYSTEMS, AND METHODS AND STORAGE MEDIUMS FOR USE THEREWITH

CROSS-REFERENCE TO RELATED APPLICATION(S)

This application relates, and claims priority, to U.S. Patent Application Ser. No. 62/587,805, filed Nov. 17, 2017, the entire disclosure of which is incorporated by reference herein in its entirety.

FIELD OF THE INVENTION

The present disclosure relates generally to the field of optical imaging and more particularly to spectrally encoded endoscopy (SEE) and/or Optical Coherence Tomography (OCT) apparatuses and systems, and methods and storage mediums for use with same. Examples of SEE applications include imaging, evaluating and characterizing/identifying biological objects or tissue, such as, but not limited to, for gastro-intestinal, cardio and/or ophthalmic applications. Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in application(s) using an apparatus or system that includes a rotary junction, an elongated extender or at least one repeater attached to the rotary junction and a rotatable probe attached to the elongated extender and/or the at least one repeater.

BACKGROUND OF THE INVENTION

Spectrally encoded endoscope (SEE) is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

Using optical fiber for imaging is getting more and more prevalent in a number of applications that may benefit from small probe size and high fidelity images. In most of these applications in order to provide reasonable field of view it is useful to rotate and/or longitudinally translate the fiber. Such rotation and/or translation of the fiber usually leads to a relatively bulky mechanism comprising an optical Rotary Junction (RJ), a rotational motor, and, sometimes, a linear stage. From one side, for the ease of use it is preferable to keep a Probe Interface Unit (PIU) inside a main system console. On the other side, for a flexible probe the rotational motion is usually imparted to the optical fiber by a flexible drive shaft disposed inside the sheath of the probe. Though this drive shaft is designed to be torsionally rigid it is still experiencing uneven wind-up in rotation leading to a Non-Uniform Rotational Distortion (NURD) compromising the final image.

In one or more instances, the shorter the flexible drive shaft is the less NURD the drive shaft exhibits. However, having a shorter flexible drive shaft may lead either to having the PIU in a separate enclosure outside of the system main console, closer to the imaging spot to reduce NURD, or to coping with an excessive NURD if a large PIU cannot be tolerated in a particular case.

In some applications, such as medical Optical Coherence Tomography (OCT) or Spectrally Encoded Endoscopy (SEE) imaging, a large and heavy PIU presents significant inconvenience for test performing personnel and a patient. For example, during cardiovascular OCT imaging, it is preferably that the PIU be placed close to the catheter entry point, sometimes right on the patient, or be held by a second person during the procedure or preparation for the procedure. In another example, a large PIU may not be tolerated for ear, nose and/or throat (ENT) imaging procedures, so a doctor should cope with inferior SEE image quality due to NURD.

Accordingly, it would be desirable to provide at least one SEE and/or OCT technique, storage medium and/or apparatus or system for use in at least one optical device, assembly or system to achieve efficient characterization and/or identification of biological object(s) or tissue, especially in a way that reduces or minimizes cost of manufacture and maintenance and/or in a way that reduces or eliminates NURD.

SUMMARY OF THE INVENTION

Accordingly, it is a broad object of the present disclosure to provide imaging (e.g., SEE) apparatuses and systems, and methods and storage mediums for use with same. It is also a broad object of the present disclosure to provide OCT devices, systems, methods and storage mediums using an interference optical system, such as an interferometer (e.g., SD-OCT, SS-OCT, etc.).

In accordance with one or more embodiments of the present disclosure, SEE apparatuses and systems, and methods and storage mediums may operate to characterize tissue type in addition to providing a morphological image to help an operator's diagnostic decision based on quantitative tissue information. In accordance with one or more embodiments of the present disclosure, SEE apparatuses and systems, and methods and storage mediums may operate to characterize biological objects other than tissue. For example, the characterization may be of a biological fluid such as blood or mucus.

One or more systems, devices, methods and storage mediums are provided herein, including, but not limited to, a rotational extender and/or repeater for rotating a fiber based optical imaging system(s) or device(s), and methods and storage mediums for use therewith. In at least one embodiment, keeping a bulky RJ away from the point of use, for example inside the main system console, is preferable, and, in one or more embodiments, use of a rotating probe extender and/or repeater to bring an optical signal to and from the imaging probe is preferable. One end of the extender is preferably connected to a system RJ while the other end of the extender preferably operates to connect to the probe. In at least one embodiment, such an extender is preferably comprised of a flexible hollow wound drive shaft containing an optical fiber(s) at its core rotating in a stationary sheath and a repeater rotary drive rotationally synchronized with the RJ motor and disposed at the probe connection end of the extender. Thus the rotary drive of the extender imparts the rotational motion on the drive shaft of the probe directly through the probe connector mitigating or eliminating the effect of additional extender length on system NURD. In one or more embodiments, a small or smaller PIU may be easier to handle, and may be positioned on a table. A probe may be made shorter by bringing the PIU closer to the point of insertion, which may reduce or eliminate NURD. In one or more embodiments, a long extender with multiple repeaters may be used to improve image quality.

One or more features of one or more embodiments of the present disclosure may also be applicable to other modes of imaging, such as ultrasound imaging known as IVUS where longer probes are routinely used leading to NURD in an image. Using a repeater close to the catheter insertion point may alleviate or address the issue in one or more embodiments.

Employing flexible drive shafts in one or more embodiments will allow for making flexible extenders as well as flexible probes. One or more embodiments may use an extender with a drive shaft made of a solid tube (for example constructed of a so called hypodermic tube made of stainless steel or of nickel-titanium alloy, also known as nitinol) without the repeater drive. Since NURD presents as image quality issues mostly for bent flexible drive shafts, if such an extender with a rigid or semi-rigid shaft may be kept relatively straight, in one or more embodiments, the torsional rigidity of the solid tube may be sufficient to minimize system NURD. Such an embodiment may be suitable for applications with flexible probes.

In torque and axial force transmission applications drive shafts are usually enclosed in stationary close fitting non-rotating sheaths to provide for rotational support, safety, and to facilitate axial motion of the shaft. These sheaths are preferably made of, or internally lined by, a low friction material, such as polytetrafluoroethylene (PTFE).

Both probe and extender connectors are preferably capable of connecting optical fiber for light signal propagation as well as of rotational motion transmission to corresponding drive shafts. Standard fiber optic connectors, such as LC connector, shall be well suited for this function. Alternatively, other standard connectors or a custom design connector may be used for this purpose.

In one or more embodiments, a repeater rotary drive of the extender is preferably a hollow shaft motor that allows an optical fiber to pass through the hollow shaft motor on the axis of rotation. Alternatively, any other design allowing to drive a probe connector, directly or indirectly, from the distal end of the extender may be employed.

For systems that use a linear pullback motion for imaging, such as cardio-vascular OCT imaging devices, additional provisions may be adapted or configured for linear motion. In one preferred embodiment (see e.g., FIGS. 3, 5, and 6) a spline-like shaft mated with a matched nut mounted on the motor shaft provides transmission of rotational motion from the repeater motor to the probe connector while allowing for a linear motion transmission from pullback stage in the console through the extender drive cable to the probe. A matching spline-like shaft/nut combination may have any suitable cross section for torque transmission, such as spline, polygon, oval, etc.

Alternatively, a pullback motion may originate directly at the repeater module utilizing, for example, rotation of the repeater motor, a rotating hollow lead screw, and an engageable stationary lead screw nut.

Yet another embodiment may incorporate into the extender a motorized linear slide that will allow the repeater to move axially performing the pullback motion. This design may address a potential non-uniform linear distortion (NULD) issue.

Yet another embodiment may comprise a long probe connected directly to the RJ and having a region along its length, preferably as close to a specimen as feasible, where a repeater may be coupled to the drive shaft of the probe and impart rotational motion on the drive shaft. In this embodiment the repeater may not be a part of a disposable probe, but may be just slid to the coupling region of the probe as needed. The coupling may be direct, such as a spline or spline-like engagement or, preferably, indirect, such as magnetic coupling that will work through the sheath.

An optical fiber coming through the extender may be a single mode fiber (SMF), for example, an SMF for OCT imaging adapted or operating to transmit light in 1310 nm range or an SMF for SEE imaging capable of transmitting wide spectrum of visible light and more in 450 nm to 850 nm. Alternative ranges of visible light may be used as well. Alternatively, it may be a dual clad fiber for multi-modal imaging.

In cases requiring very long extenders, such as when the system console and a probe are located in different rooms, where a single repeater motor may not be able to overcome drive cable friction or to avoid excessive optical fiber twisting between motors, another embodiment with multiple repeater motors positioned along the length of the extender may be preferable. In this case all the repeater motors are preferably synchronized with RJ motor rotation to prevent drive cable or optical fiber damage.

It should be noted that having a motor drive in the RJ is not necessary for one or more embodiments of the present disclosure. In yet another embodiment, the RJ does not comprise a rotary drive and is driven by the repeater rotary drive through the extender drive shaft. The physical realization of this embodiment is significantly simplified compared to one or more of the prior described embodiments of the present disclosure because the subject embodiment does not need to use or employ two motor synchronization.

One or more embodiments of the present disclosure may be used in clinical application(s), such as, but not limited to, balloon sinuplasty, sinus stenting, other sinus treatment(s), arthroscopy, use for/in the lacrimal duct, sialo endoscopy, ear research, veterinary use and research, etc. For example, at least one embodiment may be used for balloon sinuplasty to achieve success because balloon sinuplasty is a technique that relates to moving viscous mucus to a side of a passage using a balloon. As such, it is useful to be able to measure viscosity in such a situation, in any other of the aforementioned application(s), or any other application(s) that would be appreciated by those skilled in the art.

In accordance with at least another aspect of the present disclosure, the OCT and/or SEE technique(s) discussed herein may be employed to reduce the cost of at least one of manufacture and maintenance of OCT and/or SEE devices, systems and storage mediums by reducing or minimizing a number of optical components in an interference optical system, such as an interferometer.

According to other aspects of the present disclosure, one or more additional devices, one or more systems, one or more methods and one or more storage mediums using OCT and/or SEE technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, optical systems, methods and storage mediums for characterizing tissue, or an object or sample, using an imaging technique (such as, but not limited to, SEE, OCT, etc.) and using a rotational extender and/or repeater for rotating fiber based optical imaging apparatuses or systems, and methods and storage mediums for use therewith, are disclosed herein.

Figure 1A:
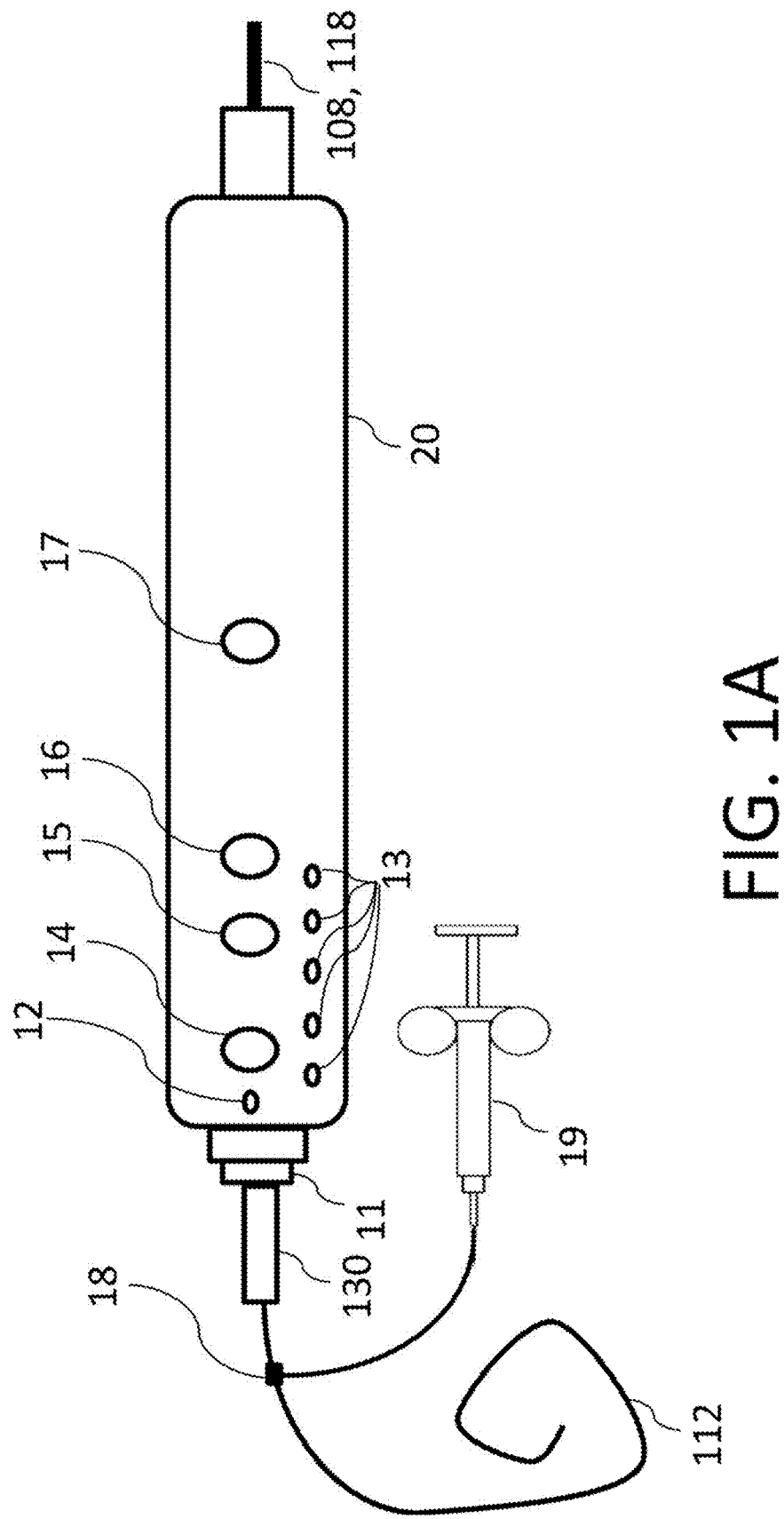
FIGS. 1A-1B are diagrams showing at least one embodiment of a drive optical controller in accordance with one or more aspects of the present disclosure.
Figure 1B:
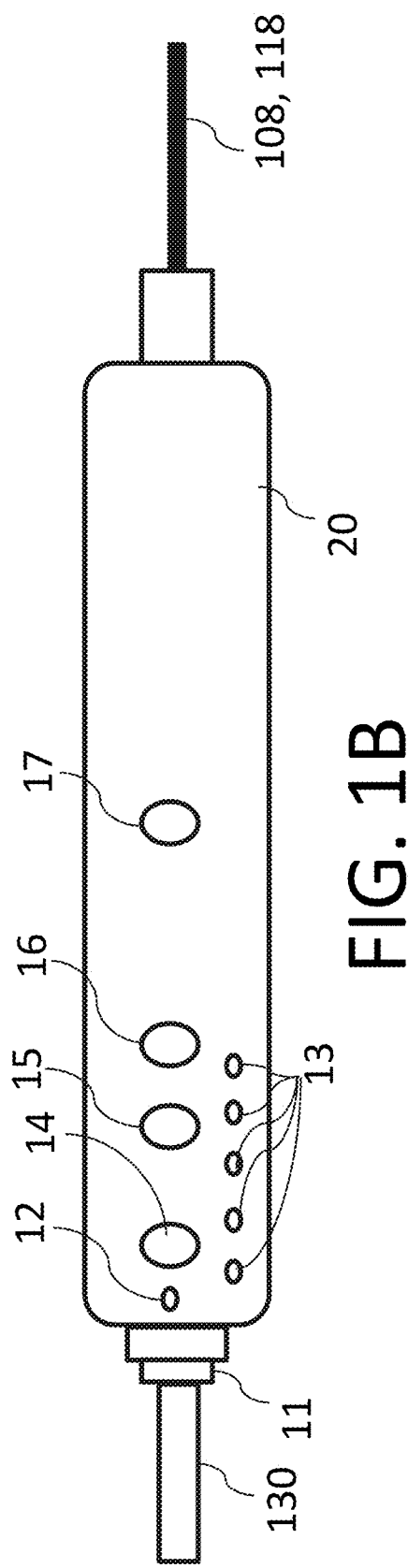

Turning now to the details of the figures, FIGS. 1A-1B show embodiments of a drive motor optical controller ("DOC") that may be used with one or more embodiments of the rotational extender and/or repeater apparatus or systems discussed herein. As shown in FIG. 1A, the DOC 20 may be used with at least one extender 33 and/or repeater 36 (shown diagrammatically—in one or more embodiments, the at least one extender 33 and/or repeater(s) 36 may be sized and shaped differently depending on the needs of one or more embodiments as further discussed below), which may be attached to the DOC 20 at an interface or connection location 11. A probe, such as the probe 112 shown in FIG. 1A and as further discussed below, may be used with the DOC 20. Preferably, the DOC 20 includes an unload button 14 that operates to allow the probe 112 to be disconnected from the extender 33 and/or repeater 36 and/or the DOC 20 (see e.g., FIG. 1B, which is the same as FIG. 1A, with the exception that the probe 112 and the needle or flushing apparatus or system 19 is disconnected from the DOC 20). While not limited to such an arrangement, in one or more embodiments, the extender 33 and/or the repeater 36 may remain with a system (e.g., the system 30 of FIG. 2, the system 30' of FIG. 3, or any other system discussed herein or component thereof (e.g., the console 31, the RJ 106, etc.), etc.), and the probe 112 may be disposable such that the probe 112 may be disconnected from a system (e.g., the system 30 of FIG. 2, the system 30' of FIG. 3, or any other system discussed herein or component thereof (e.g., the console 31, the RJ 106, etc.), etc.) and thrown away after use. The DOC 20 may also include a pullback button 15 and an advance button 16 to drive the at least one extender 33 and/or repeater 36 and/or the probe 112 as desired. The DOC 20 may also include a stop button 17 to stop the DOC 20 or one or more features thereof as desired. In one or more embodiments, the DOC 20 may include a Load Light Emitting Diode ("LED") 12 and/or may include pullback position LEDs 13 to provide useful information to a user of the DOC 20. One or more embodiments of the DOC 20 may optionally include a connection port 18 that operates to allow a needle or flushing apparatus or system 19 to be connected with a probe, such as the probe 112. Preferably, the DOC 20 operates to allow optical signals and lines to pass there through to and from a probe, such as the probe 112, and one or more other imaging components in an apparatus or system, such as, but not limited to, optical cables 108 and/or 118, which are further discussed below.

Figure 1C:
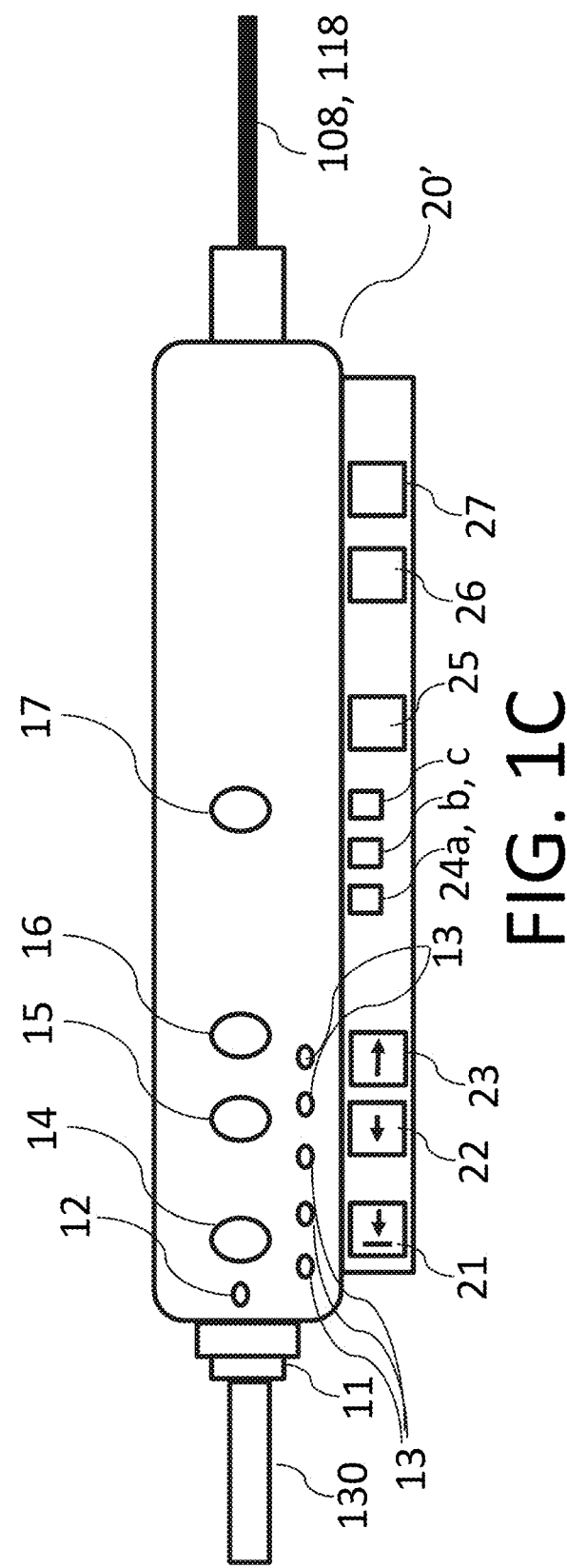
FIG. 1C is a diagram showing at least another embodiment of a drive optical controller in accordance with one or more aspects of the present disclosure.

Alternatively or additionally, a DOC, such as the DOC 20', may include additional or alternative control features. For example, the DOC 20' as shown in FIG. 1C is the same as the DOC 20 shown in FIGS. 1A-1B, with the following exceptions: The DOC 20' further includes additional control features or buttons, such as, but not limited to, the directional controls 21, 22, 23 to control the extender 33 and/or repeater 36, and/or the probe 112. In one or more embodiments, the DOC 20' may include pullback controls 26 and 27 that operate to provide a user of the DOC 20' with multiple pullback options. A scan button 25 may be included in the DOC 20'. Additionally or alternatively, LEDs, such as the LEDs 24a, b, c may be used to provide useful information to a user of the DOC 20'. For example, LED 24a may indicate that a connection exists between the DOC 20' and another optical component or component of an imaging apparatus or system. By way of another example, LED 24b may be used to indicate that power is being provided successfully to the DOC 20'. By way of a further example, LED 24c may indicate that an imaging signal is successfully being transmitted to, from and/or through the DOC 20'. One or more embodiments may employ a DOC, such as, but not limited to, the DOC 20, the DOC 20', etc. However, in one or more embodiments, a DOC may not be used or alternative components may be used.

Figure 2:
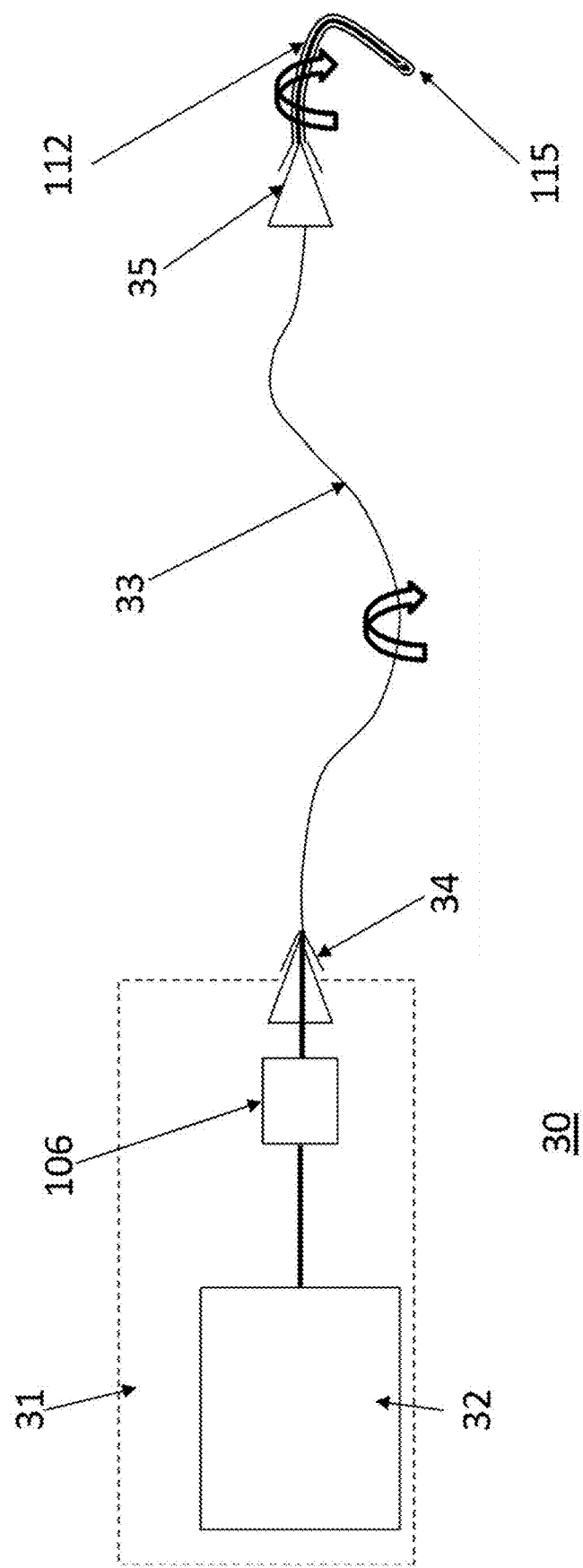
FIG. 2 is a diagram illustrating at least one embodiment of an apparatus or system using a rotating probe extender to bring an optical signal to and from an imaging probe in accordance with one or more aspects of the present disclosure.

Numerous embodiment examples of extenders and/or one or more repeaters are provided herein for rotating fiber based optical imaging apparatuses or systems. In at least one embodiment shown in FIG. 2, keeping a bulky RJ, such as, the RJ 106, away from a point of use, for example inside a main system console 31, is preferable, and, in one or more embodiments, use of a rotating probe extender, such as an extender 33 as shown in FIG. 2, and/or a repeater, such as the repeater 36 (see e.g., FIGS. 3-6 and 9-12) to bring an optical signal to and from an imaging probe (see e.g., the probe 112 shown in at least FIGS. 2-5, 8-12 and 14-15B) is preferable. As shown in FIG. 2, a system 30 may include a main console 31, an imaging system 32, a rotary junction 106, an extender 33, an extender connector 34 that operates to connect the RJ 106 to one end of the extender 33, a probe 112 (as also discussed further below), and a probe connector 35 that operates to connect the extender 33 to one end of the probe 112. One end of the extender 33 is preferably connected to a system RJ, such as the RJ 106, while the other end of the extender 33 preferably operates to connect to the probe 112.

In one or more embodiments, the console 31 may include the RJ 106, the imaging system 32, and a part of or all of the extender connector 34.

In one or more embodiments, both extender and probe connectors 34, 35 may be preferably capable of connecting optical fiber or fibers for light signal propagation as well as being capable of rotational motion transmission to corresponding drive shafts. Standard fiber optic connectors, such as, but not limited to, an LC connector, an SC connector, etc., may be well suited for such functions. Alternatively, other standard connectors or a custom design connector may be used for these purposes as desired by a user of the systems discussed herein.

Figure 12:
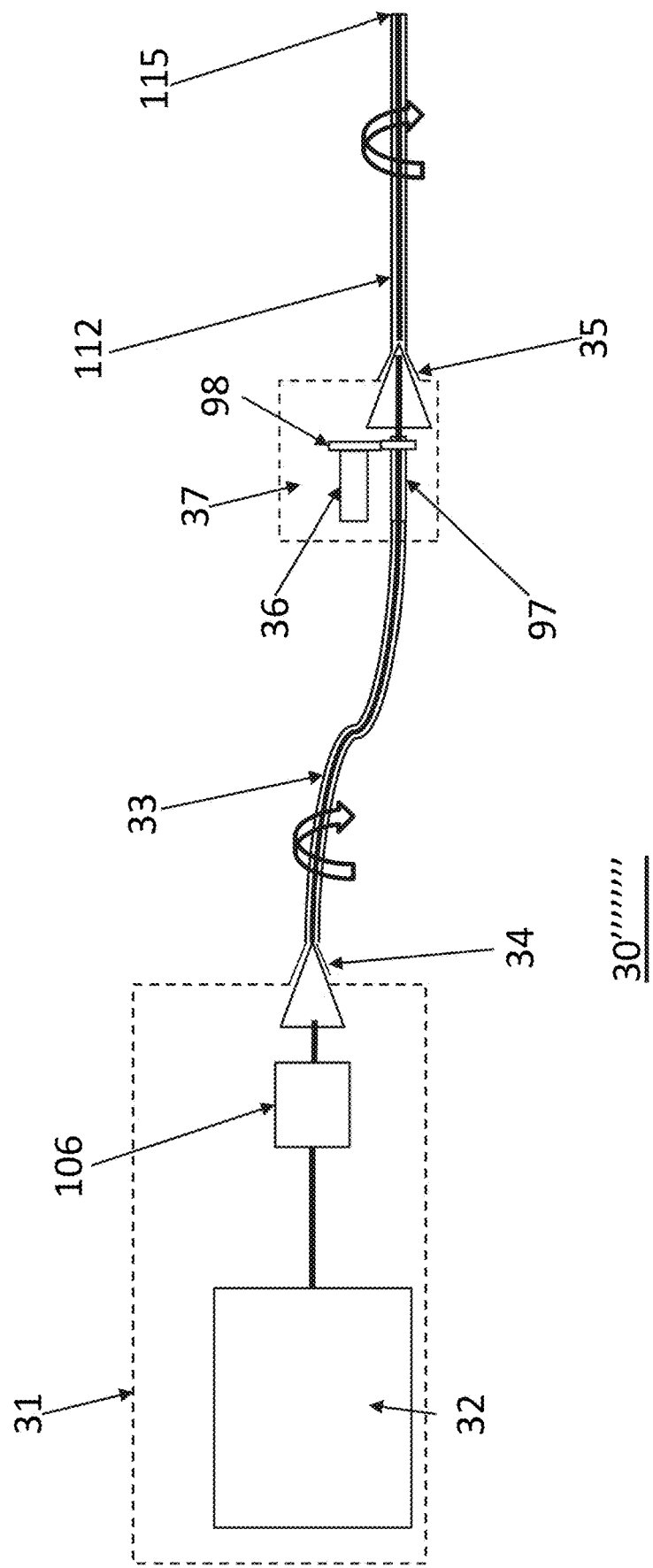
FIG. 12 is a diagram illustrating at least one embodiment of an apparatus or system using an extender and an indirect driven repeater in accordance with one or more aspects of the present disclosure.
Figure 13:
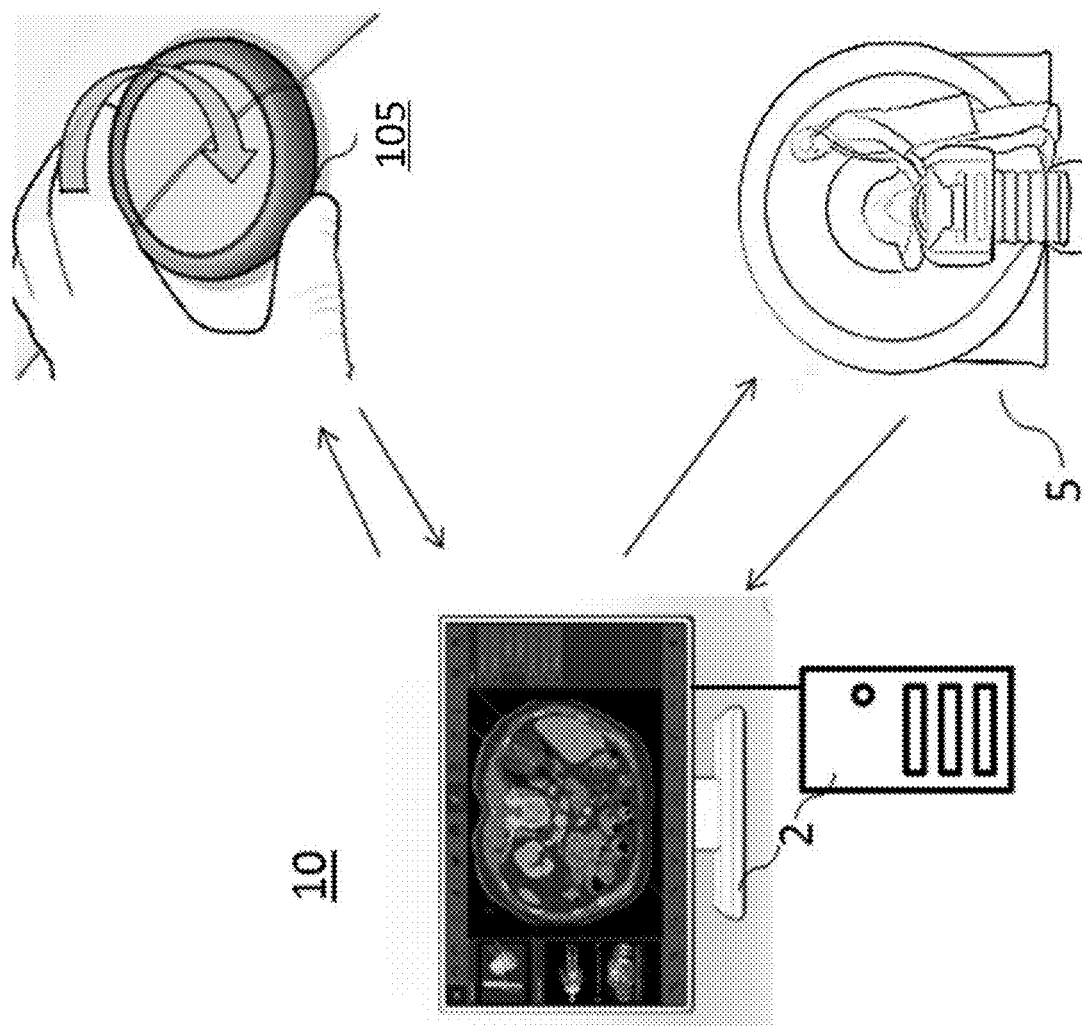
FIG. 13 is a diagram illustrating at least one embodiment of an apparatus or system using an extender and/or repeater in accordance with one or more aspects of the present disclosure.
Figure 13:
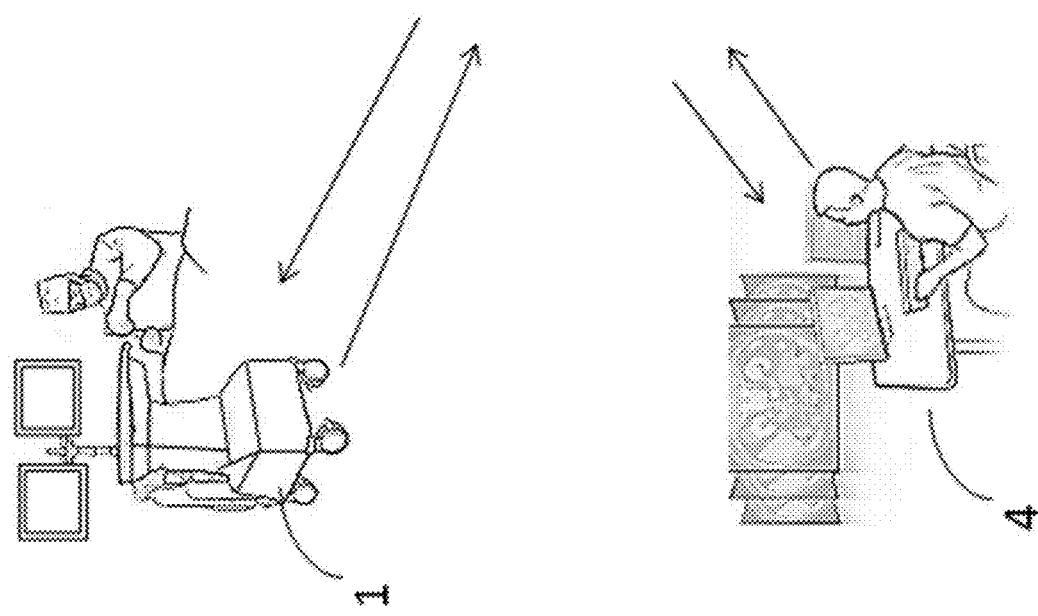

In one or more embodiments, the imaging system 32 may include any of the imaging components discussed herein. For example, in one or more embodiments (see e.g., FIGS. 13-18), an imaging system 32 may include one or more of the following: a light source 101, optic fiber(s) (see e.g., fibers 104, 108, 118, etc. discussed below), at least one detector such as a spectrometer 120, the ROJ 106 or part of the ROJ 106, a processor or computer (see e.g., the processor computer 2 in FIG. 13; the processor or computer console 1200, the processor computer 1200', etc. in at least FIGS. 14-15B and FIGS. 17-18; etc.), a motor 140, a medical console 1 (see e.g., FIG. 13), a scanning device (e.g., a CT scanner 5 as shown in FIG. 13), a deflector 117 (discussed below), etc. Combinations of such components or other components discussed herein may be made in one or more embodiments as desired depending on the medical procedure, imaging technique or procedure, and/or other consideration(s) of a user of any of the imaging apparatuses or systems discussed herein (see e.g., apparatus or system 30 of FIG. 2, apparatus or system 30' of FIG. 3, apparatus or system 30" of FIG. 4, apparatus or system 30'" of FIG. 5, apparatus or system 30"" of FIG. 8, apparatus or system 30'"'' of FIG. 9, apparatus or system 30"""" of FIG. 10, apparatus or system 30""""' of FIG. 11, apparatus or system 30"""""" of FIG. 12, system 10 of FIG. 13, system 100 of FIG. 14, system 100' of FIG. 15A, system 100" of FIG. 15B, system 1000 of FIG. 16, etc.).

Preferably, the rotary junction 106 operates to rotate the extender 33 via the extender connector 34 and the probe 112 via the probe connector 35 such that a distal end 115 of the probe 112 rotates to obtain one or more desired images of a target (e.g., a sample, an object, a patient, in vivo tissue, etc.). Preferably, the RJ 106, the extender 33 and the probe 112 are connected such that rotation of the rotating portion of the RJ 106, rotation of the extender 33 and rotation of the probe 112 are synchronized or are substantially synchronized to reduce or avoid NURD and/or to prevent fiber breakage.

One or more features of one or more embodiments of the present disclosure may also be applicable to other modes of imaging, such as ultrasound imaging known as IVUS where longer probes are routinely used leading to NURD in an image (e.g., a slip joint may be used to transfer the electric signals in at least one IVUS embodiment). As such, one or more features discussed herein are advantageous to reduce or avoid NURD. For example, using a repeater, such as the repeater or repeater motor 36 discussed herein, close to a catheter insertion point may alleviate or address the issue of NURD in one or more embodiments.

Figure 3:
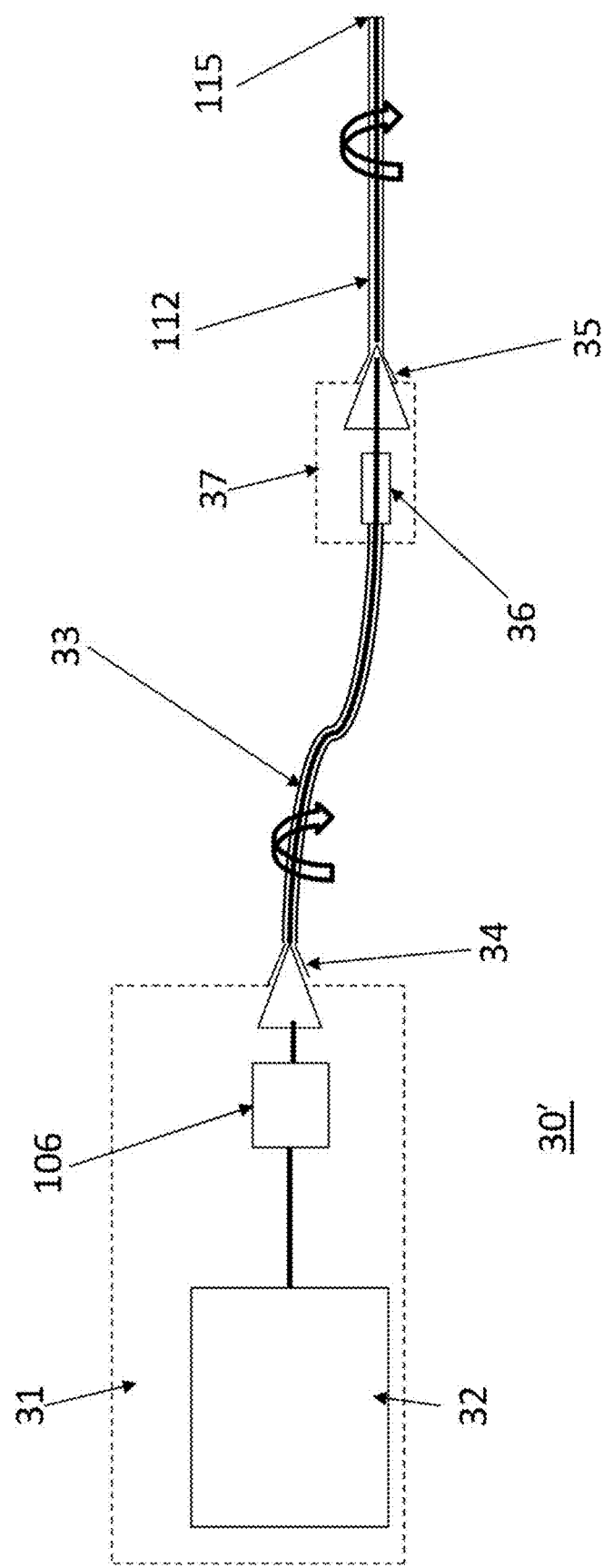
FIG. 3 is a diagram illustrating at least one embodiment of an apparatus or system using a rotating probe extender and repeater to bring an optical signal to and from an imaging probe in accordance with one or more aspects of the present disclosure.

Additionally or alternatively, as shown in FIG. 3, in at least one embodiment, a system 30' may include an extender, such as the extender 33, that may include a flexible hollow drive shaft including optical fiber(s) therein rotating with the extender 33 and a probe interface unit ("PIU") 37 that may include a repeater or repeater motor 36 and part of or all of the probe connector 35. In this embodiment employing the extender 33 and the repeater 36, no pullback may be used or required to reduce or avoid NURD while maintaining synchronization or substantial synchronization of the rotation of the extender 33, the probe 112 and the rotating part of the ROJ 106. In one or more embodiments, the extender 33 may be preferably comprised of a flexible hollow wound drive shaft containing an optical fiber(s) at its core rotating in a stationary sheath and a repeater rotary drive, such as the repeater 36, rotationally synchronized with the RJ 106, and/or a motor for same (see e.g., the motor 140 discussed herein below), and disposed at the probe connection end 34 of the extender 33. The system 30' may be the same as, or may include one or more of the same components as, system 30, with the exceptions discussed herein such that descriptions of the same or similar reference number elements shown in the subject systems shall not be repeated.

In one or more embodiments, the repeater drive 36 of the extender 33 imparts the rotational motion on the drive shaft of the probe 112 directly through the probe connector 35 mitigating or eliminating the effect of additional extender length on system NURD. In one or more embodiments, a small or smaller PIU 37 may be easier to handle, and may be positioned on a table. A probe, such as the probe 112, may be made shorter by bringing the PIU 37 closer to the point of insertion, which may reduce or eliminate NURD. In one or more embodiments, a long extender with multiple repeaters may be used to improve image quality.

Figure 4:
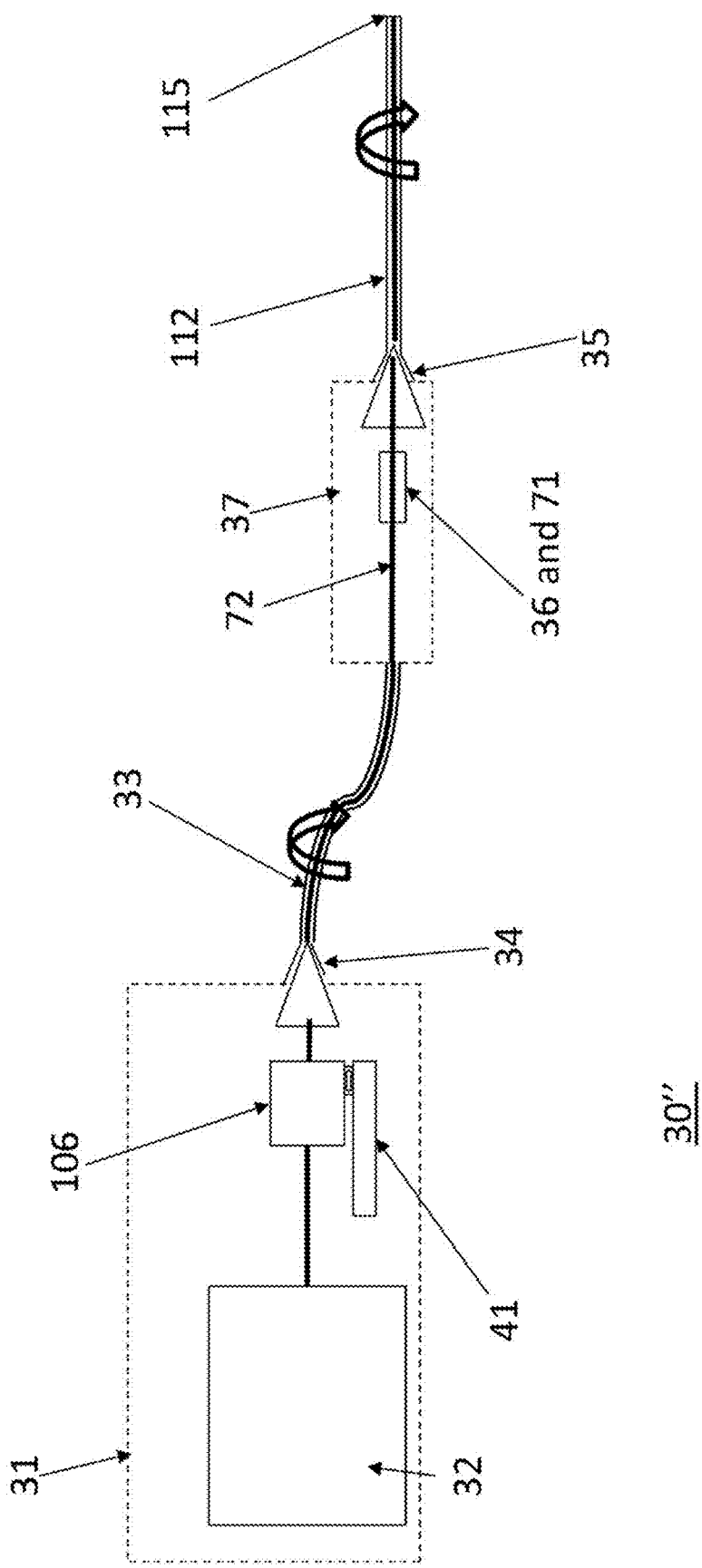
FIG. 4 is a diagram illustrating at least one embodiment of an apparatus or system using a rotating probe extender and repeater to bring an optical signal to and from an imaging probe having a pullback feature in accordance with one or more aspects of the present disclosure.

Additionally or alternatively, as best seen in FIG. 4, in at least one embodiment, a system 30" may include an extender, such as the extender 33, that may be comprising of a flexible hollow wound drive shaft containing an optical fiber or fibers at its core rotating in a stationary sheath and a repeater rotary drive rotationally synchronized with the RJ motor and disposed at the probe connection end of the extender (see e.g., FIG. 4), and may be designed to provide or work with pullback (e.g., a pullback stage 41 may be included in the console 31 as shown in FIG. 4). The probe interface unit 37 may further include a spline-like nut 71 being use with the repeater or the repeater motor 36, and may also include a spline-like shaft 72. In one or more embodiments, the rotary drive of the extender imparts the rotational motion on the drive shaft of the probe directly through the probe connector mitigating or eliminating the effect of additional extender length on system NURD. In one or more embodiments, a small or smaller PIU may be easier to handle, and may be positioned on a table. A probe may be made shorter by bringing the PIU closer to the point of insertion, which may reduce or eliminate NURD. In one or more embodiments, a long extender with multiple repeaters may be used to improve image quality. The system 30" may be the same as, or may include one or more of the same components as, system 30 and/or system 30', with the exceptions discussed herein such that descriptions of the same or similar reference number elements shown in the subject systems shall not be repeated.

Employing flexible drive shafts in one or more embodiments allows for making flexible extenders 33 as well as flexible probes 112. In one or more embodiments, at least one repeater 36 of an elongated extender 33 may be disposed in a proximity to, or is adjacent to, a signal transmitting connector of the elongated extender 36, and a portion of a rotatable drive shaft proximal, near or adjacent to the at least one repeater drive 36 may be a low-flexing or substantially rigid tube (e.g., a tube that is rigid, a tube that will break or be deformed if bent, a tube that will be permanently deformed if bent, etc.) of approximately oval cross-section rigidly attached to the signal transmitting connector of the elongated extender. In one or more embodiments, the low-flexing or substantially rigid tube of the elongated extender 33 may have an axially sliding support disposed in proximity to, or adjacent or close to, the signal transmitting connector of the elongated extender 33, the axially sliding support operating to allow the low-flexing or substantially rigid tube to spin freely and to restrict or prevent one or more cross-axis displacements.

Figure 5:
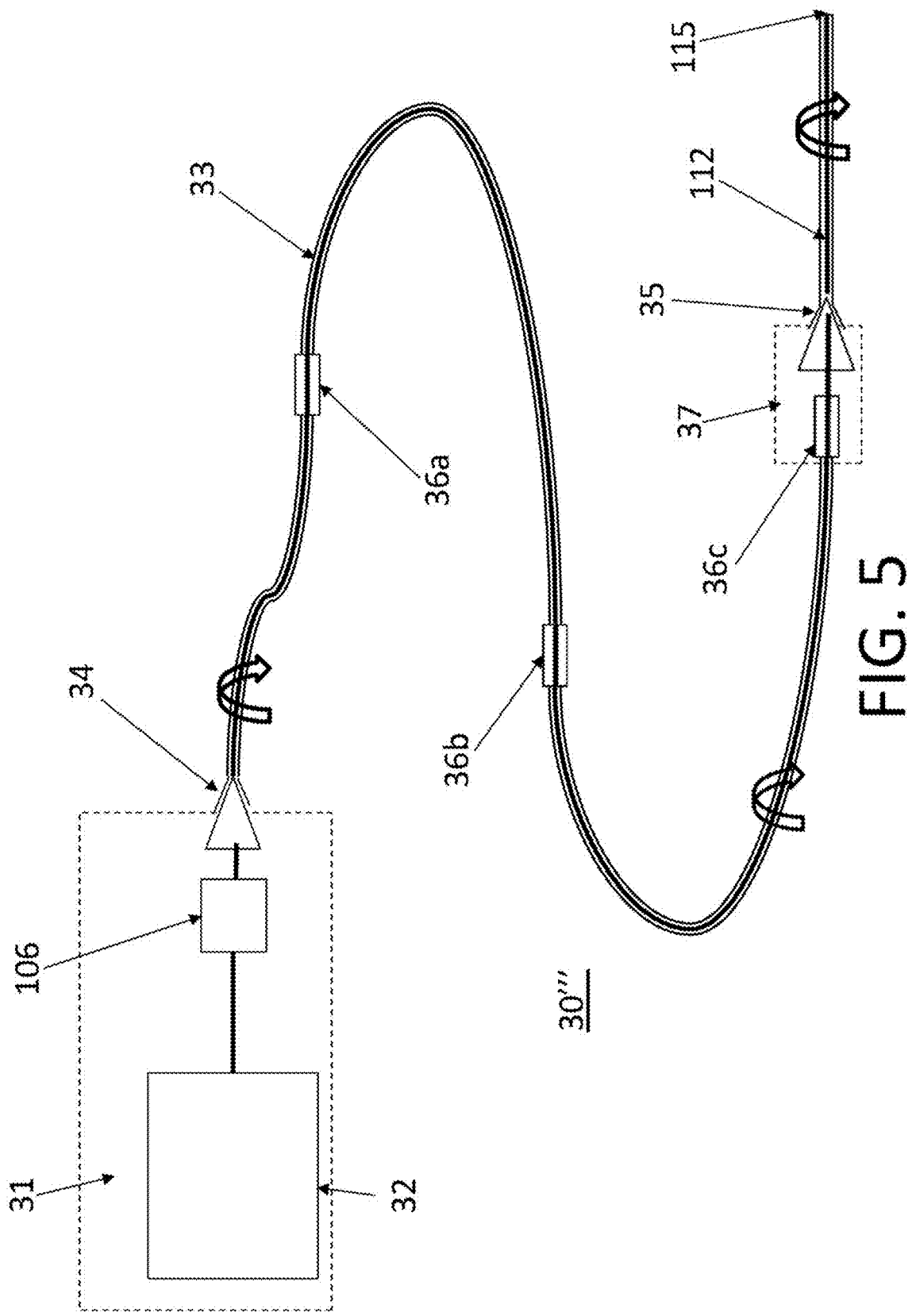
FIG. 5 is a diagram illustrating at least one embodiment of an apparatus or system using a rotating probe extender and repeaters to bring an optical signal to and from an imaging probe in accordance with one or more aspects of the present disclosure.

In cases requiring very long extenders, such as when the system console 31 and the probe 112 are located in different rooms, where a single repeater motor 36 may not be able to overcome drive cable friction or to avoid excessive optical fiber twisting between motors 36, another embodiment with multiple repeaters or repeater motors 36a, 36b, 36c positioned along the length of the extender 33 may be preferable as shown, for example, in FIG. 5. In this case all the repeaters or repeater motors 36a, 36b, 36c are preferably synchronized with rotation of the RJ 106 and/or the motor 140 controlling rotation of the RJ 106 to prevent drive cable or optical fiber damage. The probe interface unit 37 may include the last repeater or repeater motor 36c that is located near the probe connector 35. The system 30''' may be the same as, or may include one or more of the same components as, system 30, system 30', and/or system 30", with the exceptions discussed herein such that descriptions of the same or similar reference number elements shown in the subject systems shall not be repeated.

It should be noted that having a motor drive 140 (also referred to herein as a motion control unit 140) in or attached to the RJ 106 is not necessary for one or more embodiments of the present disclosure. In yet another embodiment, the RJ 106 does not comprise a rotary drive and is driven by the repeater rotary drive 36 through the drive shaft of the extender 33. The physical realization of this embodiment is significantly simplified compared to one or more of the prior described embodiments of the present disclosure because the subject embodiment does not need to use or employ two motor synchronization.

Figure 6:
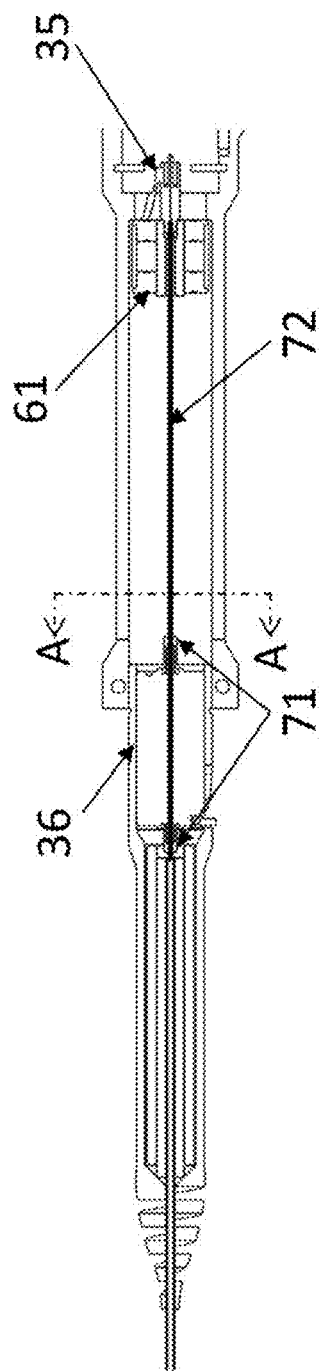
FIG. 6 is a diagram illustrating at least one embodiment of a repeater end of an extender that operates to achieve pullback in accordance with one or more aspects of the present disclosure.
Figure 7:
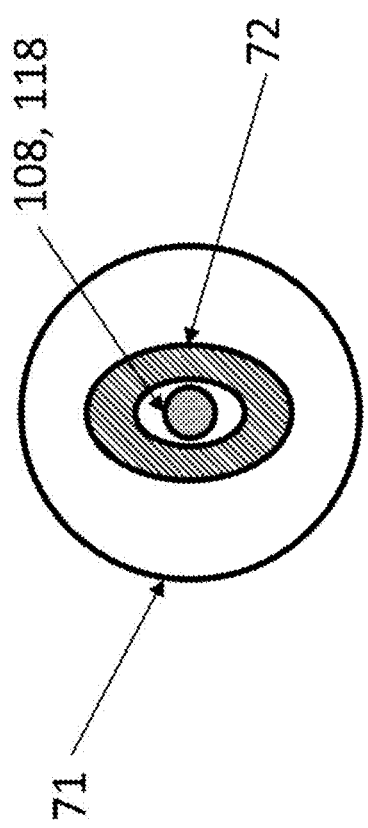
FIG. 7 is a cross-sectional view along line A-A of FIG. 6 in accordance with one or more aspects of the present disclosure.

For systems that use a linear pullback motion for imaging, such as cardio-vascular OCT imaging devices, additional provisions may be adapted or configured for linear motion. In one or more embodiments (see e.g., FIGS. 4, 6, and 7) the spline-like shaft 72 discussed above mated with a matched nut, such as the spline-like nut 71, mounted on the motor shaft provides transmission of rotational motion from the repeater or repeater motor 36 to the probe connector 35 while allowing for a linear motion transmission from a pullback stage (e.g., the pullback stage 41) in the console 31 through the drive cable of the extender 33 to the probe 112. As best seen in FIG. 6, the repeater or repeater drive/motor 36 may include the spline-like shaft 72 extending there through, and the spline-like shaft 72 may connect to, or pass through, the spline-like nut(s) 71. The spline-like shaft 72 may connect to the probe connector 35. The repeater or repeater drive 36 and/or the probe interface unit 37 may include a connector support 61 that operates to achieve or facilitate connection between the spline-like shaft 72 and the probe connector 35. A matching spline-like shaft/nut combination 71, 72 may have any suitable cross section for torque transmission, such as spline, polygon, oval (see e.g., FIG. 7), etc. For example, in one or more embodiments the spline-like shaft 72 may be manufactured by controlled deforming of a stainless steel tube, also known as a hypodermic tube. As shown in FIG. 7, optic fibers, such as, but not limited to, fibers 108, 118, etc. may pass through the spline-like shaft/nut combination 71, 72. The spline-like shaft 72 may pass through the spline-like nut(s) 71 (as shown in FIGS. 6-7).

An optical fiber (such as, but not limited to, fibers 108, 118, etc.) coming through the extender 33 may be a single mode fiber (SMF), for example, an SMF for OCT imaging adapted or operating to transmit light in 1310 nm range or an SMF for SEE imaging capable of transmitting wide spectrum of visible light and more in 450 nm to 850 nm. Alternative ranges of visible light may be used as well. Alternatively, one or more fibers passing through the extender 33 may be a dual clad fiber for multi-modal imaging.

Figure 8:
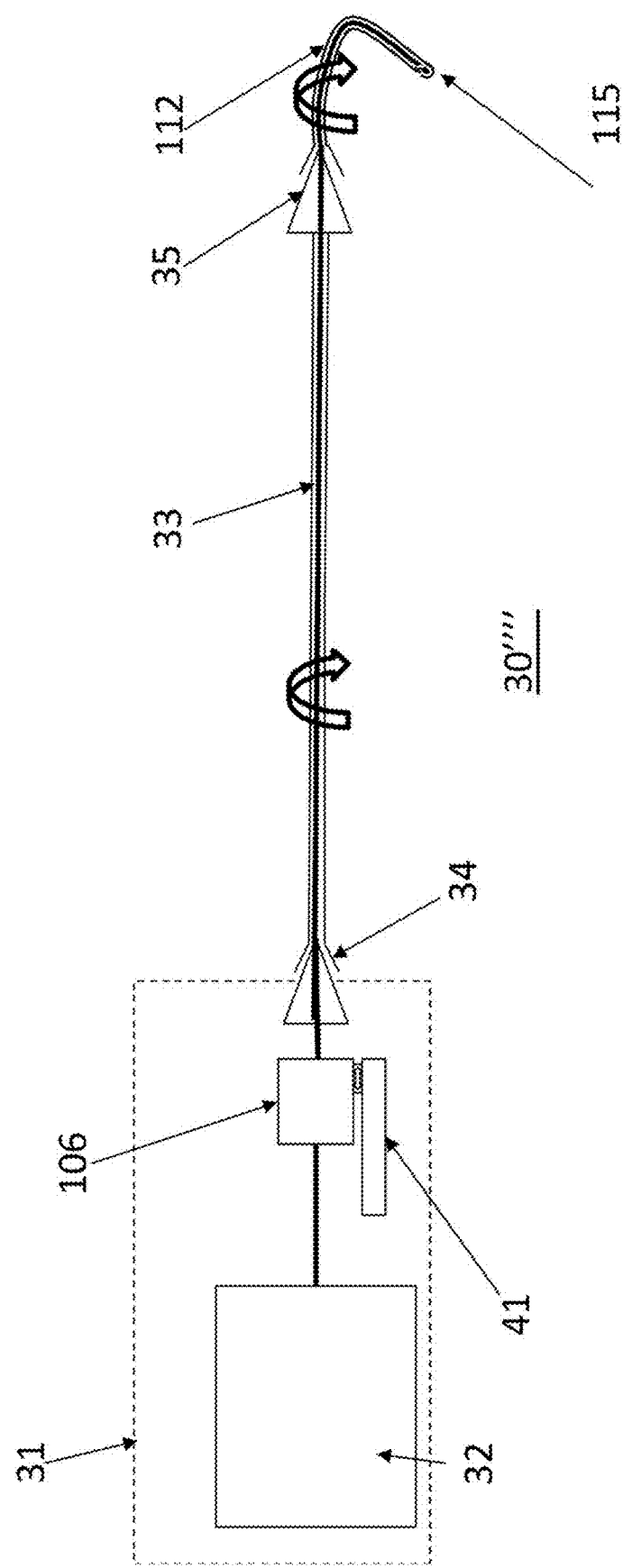
FIG. 8 is a diagram illustrating at least one embodiment of an apparatus or system using a straight extender without a repeater to bring an optical signal to and from an imaging probe in accordance with one or more aspects of the present disclosure.

Alternatively or additionally, as best shown in FIG. 8, one or more embodiments may use an extender 33 with a drive shaft made of a solid tube (for example constructed of a so-called hypodermic tube made of stainless steel or of nickel-titanium alloy, also known as nitinol) without the repeater or the repeater drive 36. Since NURD presents as image quality issues mostly for bent flexible drive shafts, if such an extender 33 with a rigid or semi-rigid shaft may be kept relatively straight, in one or more embodiments, the torsional rigidity of the solid tube may be sufficient to reduce and/or minimize system NURD. Such an embodiment may by suitable for applications with flexible probes (see e.g., the probe 112 in FIG. 8). The system 30'''' may be the same as, or may include one or more of the same components as, system 30, system 30', system 30'' and/or system 30''', with the exceptions discussed herein such that descriptions of the same or similar reference number elements shown in the subject systems shall not be repeated.

Figure 9:
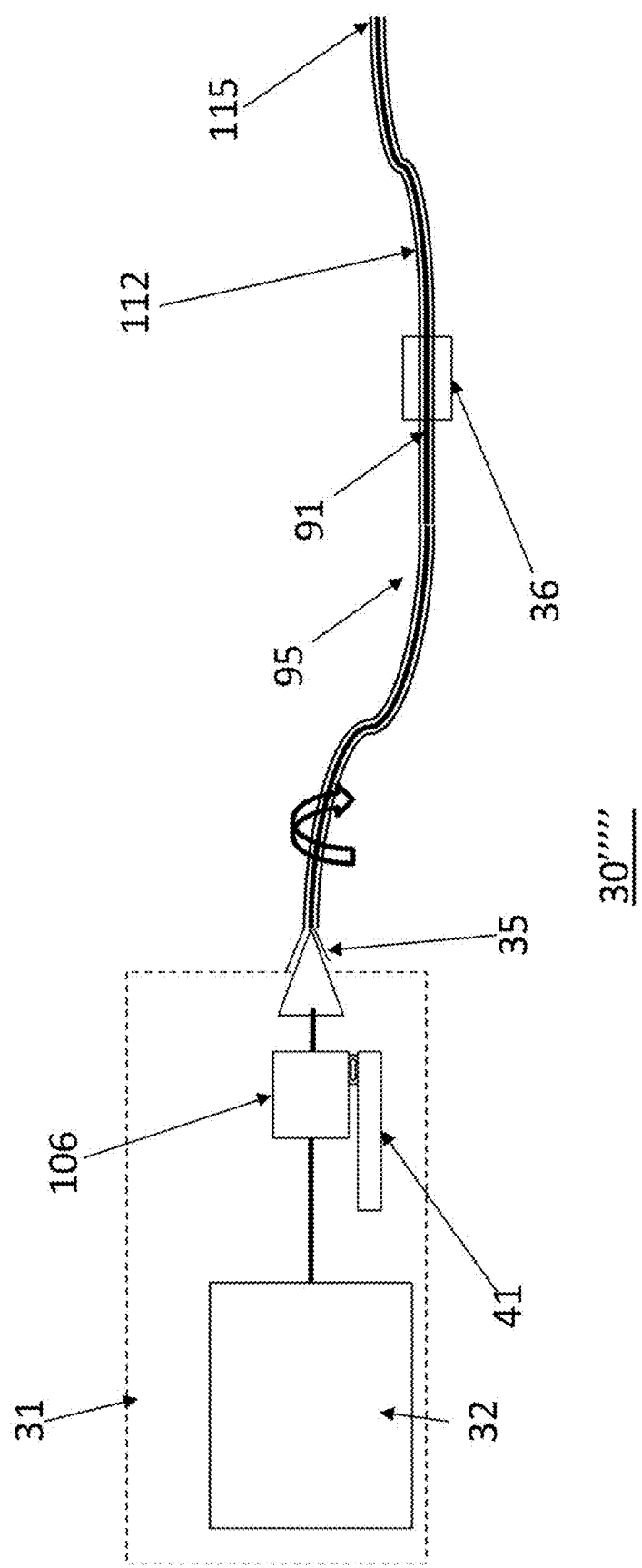
FIG. 9 is a diagram illustrating at least one embodiment of an apparatus or system using a long probe with a slide-on repeater having a pullback feature in accordance with one or more aspects of the present disclosure.

Yet another embodiment such as the system 30'''' may comprise a long probe, such as the probe 112, connected directly to the RJ 106 (e.g., no extender 33 included) and having a region along its length, preferably as close to a target (e.g., an object, a specimen, a patient, etc.) as feasible, where a repeater, such as the repeater 36 shown in FIG. 9, may be coupled to the drive shaft of the probe 112 and impart rotational motion on the drive shaft of the probe 112. In this embodiment, the repeater 36 may not be a part of a disposable probe, such as the probe 112, but may be slid to the coupling region of the probe 112 (e.g., slid on the probe 112, slid off the probe 112, slid along the probe 112, etc.) as needed. The coupling may be direct, such as a spline or spline-like engagement or, preferably, indirect, such as magnetic coupling that may work through the sheath (see e.g., FIG. 9). The long probe 112 operates to work with the slide-on repeater 36, with the pullback stage 41. The system 30'''' may be the same as, or may include one or more of the same components as, system 30, system 30', system 30'', system 30''' and/or system 30'''', with the exceptions discussed herein such that descriptions of the same or similar reference number elements shown in the subject systems shall not be repeated.

Additionally, in one or more embodiments involved in torque and axial force transmission applications, drive shafts may be enclosed in stationary close fitting non-rotating sheaths (see e.g., the sheath 95 around or on the probe 112 shown diagrammatically in FIG. 9) to provide for rotational support, safety, and to facilitate axial motion of the shaft. These sheaths may preferably be made of, or internally lined by, a low friction material, such as polytetrafluoroethylene (PTFE).

Figure 10:
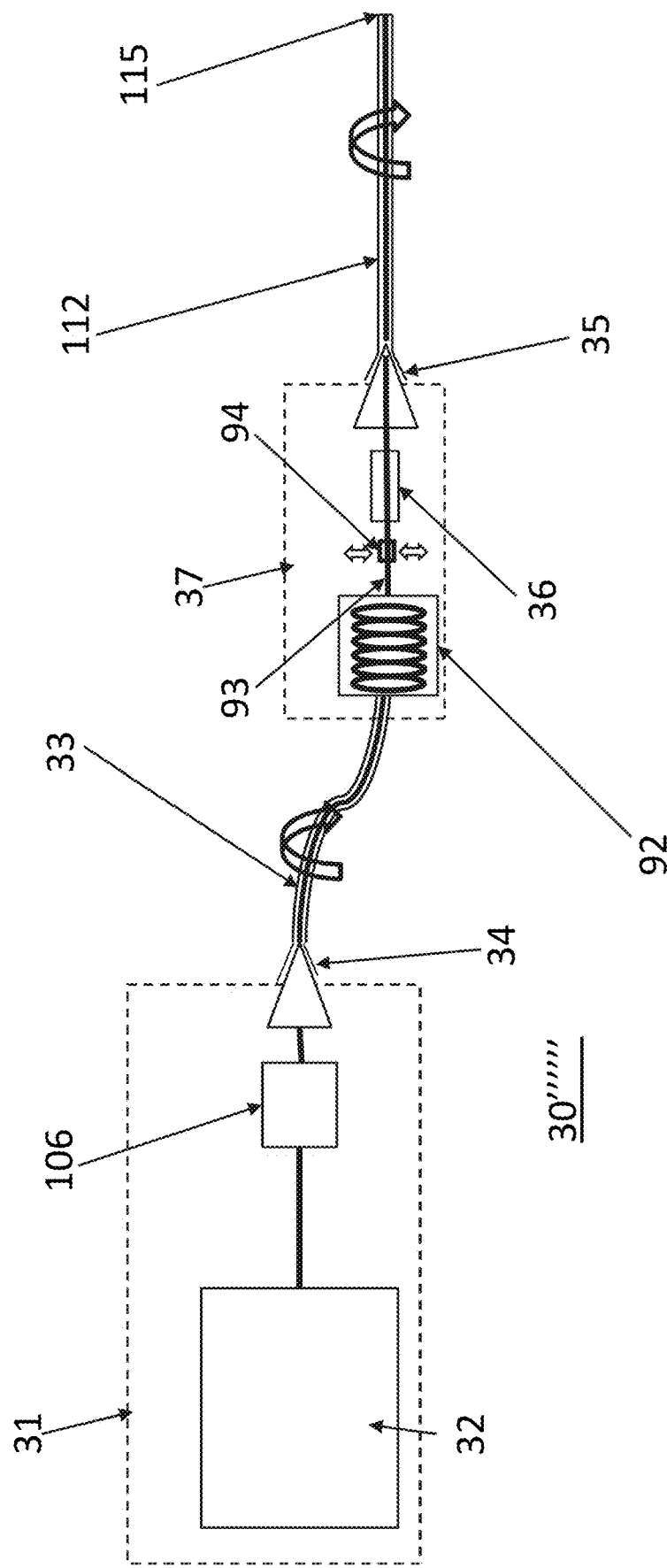
FIG. 10 is a diagram illustrating at least one embodiment of an apparatus or system using an extender and a repeater with repeater pullback in accordance with one or more aspects of the present disclosure.

Alternatively, a pullback motion may originate directly at the repeater or repeater module 36 utilizing, for example, rotation of the repeater or repeater motor 36, a rotating hollow lead screw, and an engageable stationary lead screw nut. For example, in at least one embodiment as shown in FIG. 10, a system 30''''' may use a pullback motion that originates directly at the repeater module 36 (also referred to as repeater pullback) in the probe interface unit 37, for example, by utilizing rotation of the repeater or repeater motor 36, a rotating hollow lead screw (see e.g., lead screw 93 of FIG. 10), and an engageable stationary lead screw nut (see e.g., engageable lead screw nut 94 of FIG. 10). The probe interface unit 37 may further include a core portion accumulator 92 to further assist in achieving a pullback motion. The system 30''''' may be the same as, or may include one or more of the same components as, system 30, system 30', system 30'', system 30''', system 30'''' and/or system 30''''', with the exceptions discussed herein such that descriptions of the same or similar reference number elements shown in the subject systems shall not be repeated.

Figure 11:
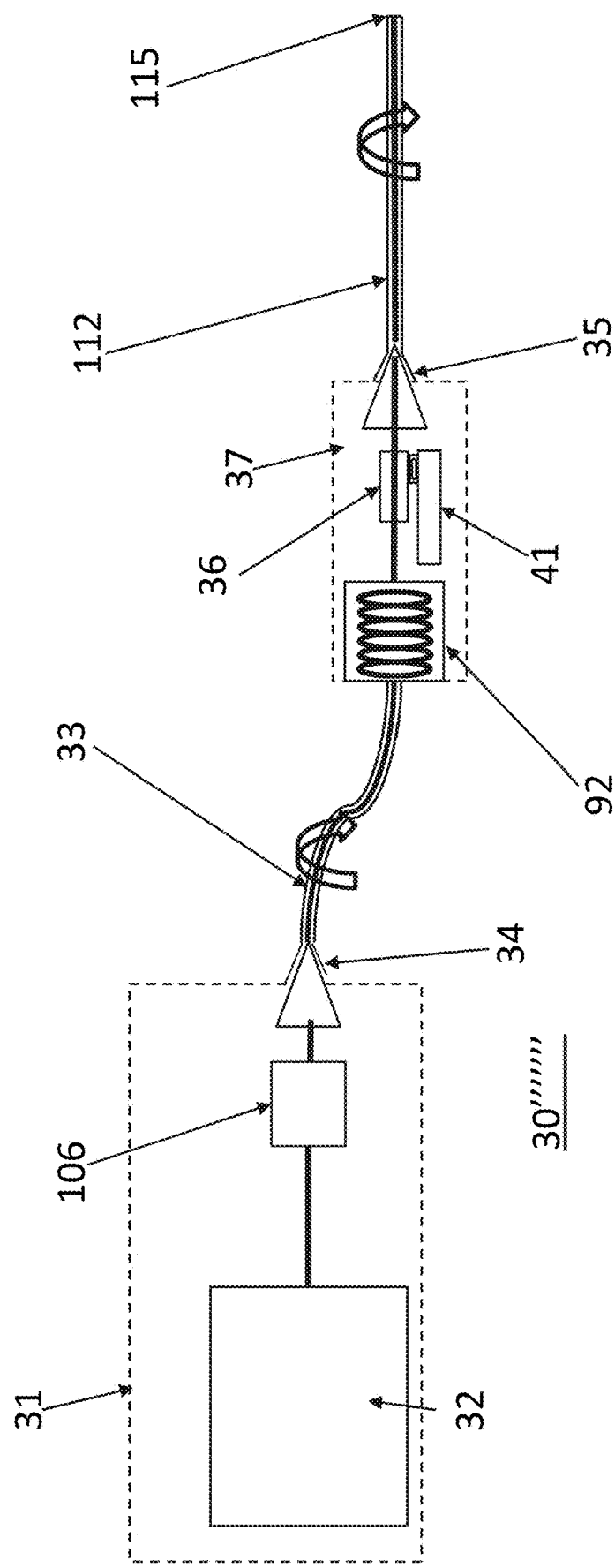
FIG. 11 is a diagram illustrating at least one embodiment of an apparatus or system using an extender and a repeater with repeater pullback stage being located in a probe interface unit in accordance with one or more aspects of the present disclosure.

Yet another embodiment may incorporate into the extender 33 a motorized linear slide that will allow the repeater 36 to move axially performing the pullback motion. This design may address a potential non-uniform linear distortion (NULD) issue. For example, as best seen in FIG. 11, a system 30'''''' may include the pullback stage 41 in the probe interface unit 37 and may further include a core portion accumulator, such as the core portion accumulator 92, in the PIU 37. The system 30'''''' may be the same as, or may include one or more of the same components as, system 30, system 30', system 30'', system 30''', system 30'''', system 30''''' and/or system 30''''', with the exceptions discussed herein such that descriptions of the same or similar reference number elements shown in the subject systems shall not be repeated.

In one or more embodiments as shown in FIGS. 3-11, a repeater rotary drive 36 of the extender 33 may preferably be a hollow shaft motor that allows an optical fiber to pass through the hollow shaft motor on or substantially on, or parallel to or substantially parallel to, the axis of rotation. Alternatively, any other design operating to drive a probe connector, such as the probe connector 35, directly or indirectly, from the distal end of the extender 33 may be employed. The repeater or repeater motor 36 may be indirectly connected to a repeater hollow shaft 97 via a gear 98, for example, as shown in FIG. 12. Such components may be included in the PIU 37.

As shown diagrammatically in FIG. 13, a medical device 1, 105, 5, etc. may be used with one or more of the extender and/or repeater apparatuses or systems discussed herein. For example, the system 2 may communicate with the image scanner 5 to request information for use in a medical imaging procedure (e.g., in a needle guidance planning and/or performance procedure), such as, but not limited to, bed or slice positions, and the image scanner 5 may send the requested information along with the images to the system 2 once a clinician uses the image scanner 5 to obtain the information via scans of the patient. By way of another example, the system 2 may communicate and be used with a guidance device (also referred to as a locator device) 105 (such as an image-plane localizer that may be a patient-mount device and may be rotated as shown to help locate to biological object, such as a lesion or tumor). The aforementioned embodiments shown in FIGS. 1-12 may be employed in or with the system 10, the computer or system 2, the medical device 1, the device 105, the scanner 5, etc., to obtain information from the patient when conducting medical procedures. The system 2 may further communicate with a PACS 4 to send and receive images of a patient to facilitate and aid in the medical procedure planning and/or performance. Once the plan is formed, a clinician may use the system 2 along with a medical device (e.g., an ablation device using the extender and/or repeater technology discussed herein, a biopsy device using the extender and/or repeater technology discussed herein, an OCT device using the extender and/or repeater technology discussed herein, a SEE device using the extender and/or repeater technology discussed herein, etc.) 1 to consult a chart or plan (e.g., for needle guidance, for ablation, for biopsy, for a medical procedure, etc.) to understand the shape and/or size of the targeted biological object to undergo the medical procedure (e.g., ablation, biopsy, etc.). Each of the medical device 1, the system 2, the guidance device 105, the PACS 4 and the scanning device 5 may communicate in any way known to those skilled in the art, including, but not limited to, directly (via a communication network) or indirectly (via one or more of the other devices 1, 105 or 5; via one or more of the PACS 4 and the system 2; via clinician interaction; etc.). In one or more embodiments as discussed herein, the guidance device 105 may communicate wirelessly with one or more of the following: the medical device 1, the system 2, the PACS 4, and the scanning device 5. Preferably, in one or more embodiments, the guidance device 105 communicates wirelessly with at least the system 2 or any other processor operating to interact with the guidance device 105 to perform the needle guidance planning and/or performance.

Figure 14:
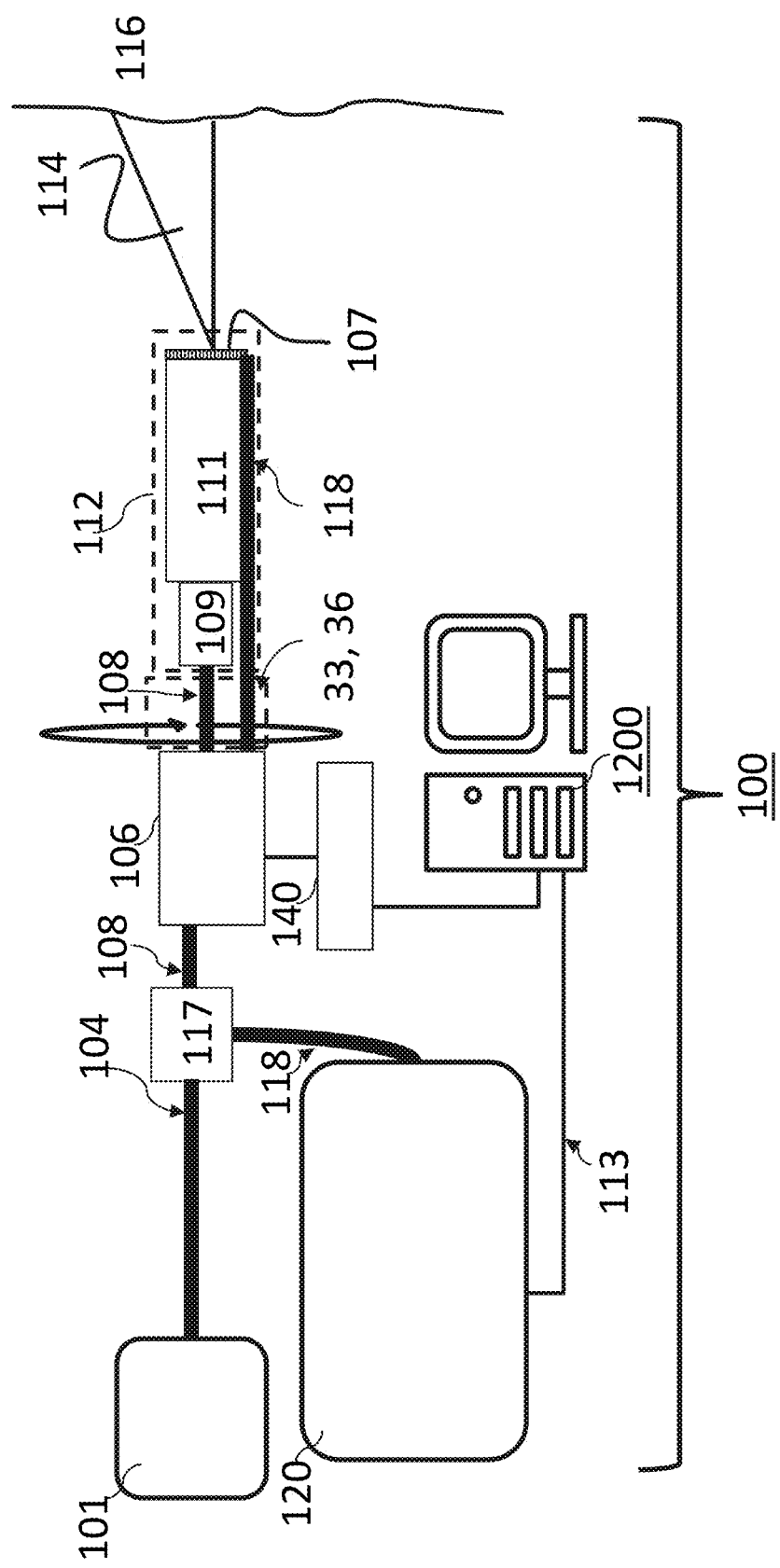
FIG. 14 is a schematic diagram showing an embodiment of a system for performing imaging and/or needle guidance planning and/or performance, and/or for performing an imaging and/or medical procedure, in accordance with one or more aspects of the present disclosure.
Figure 15A:
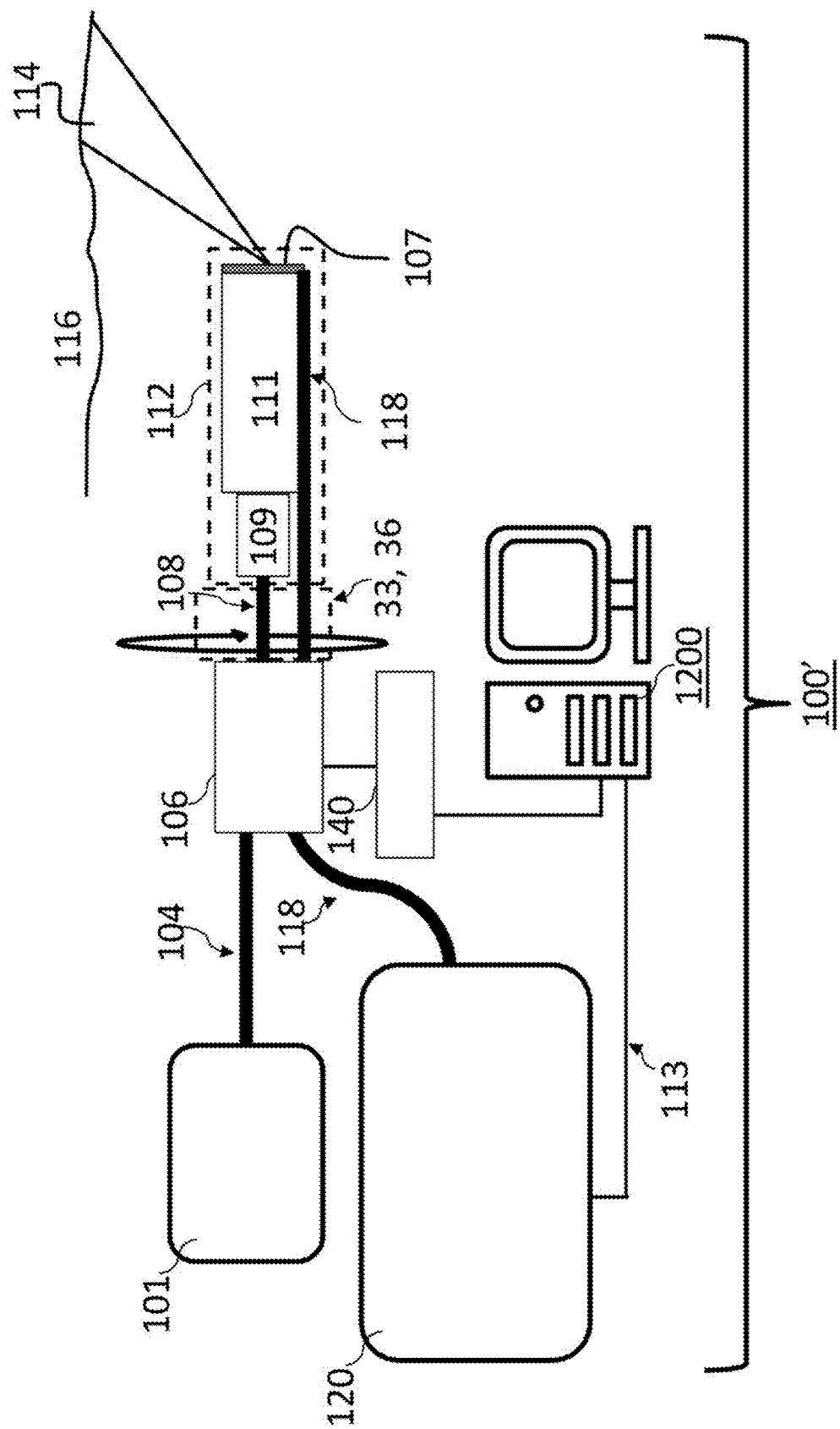
FIGS. 15A-15B are diagrams illustrating at least two embodiments of an apparatus or system using an extender and/or repeater in accordance with one or more aspects of the present disclosure.
Figure 15B:
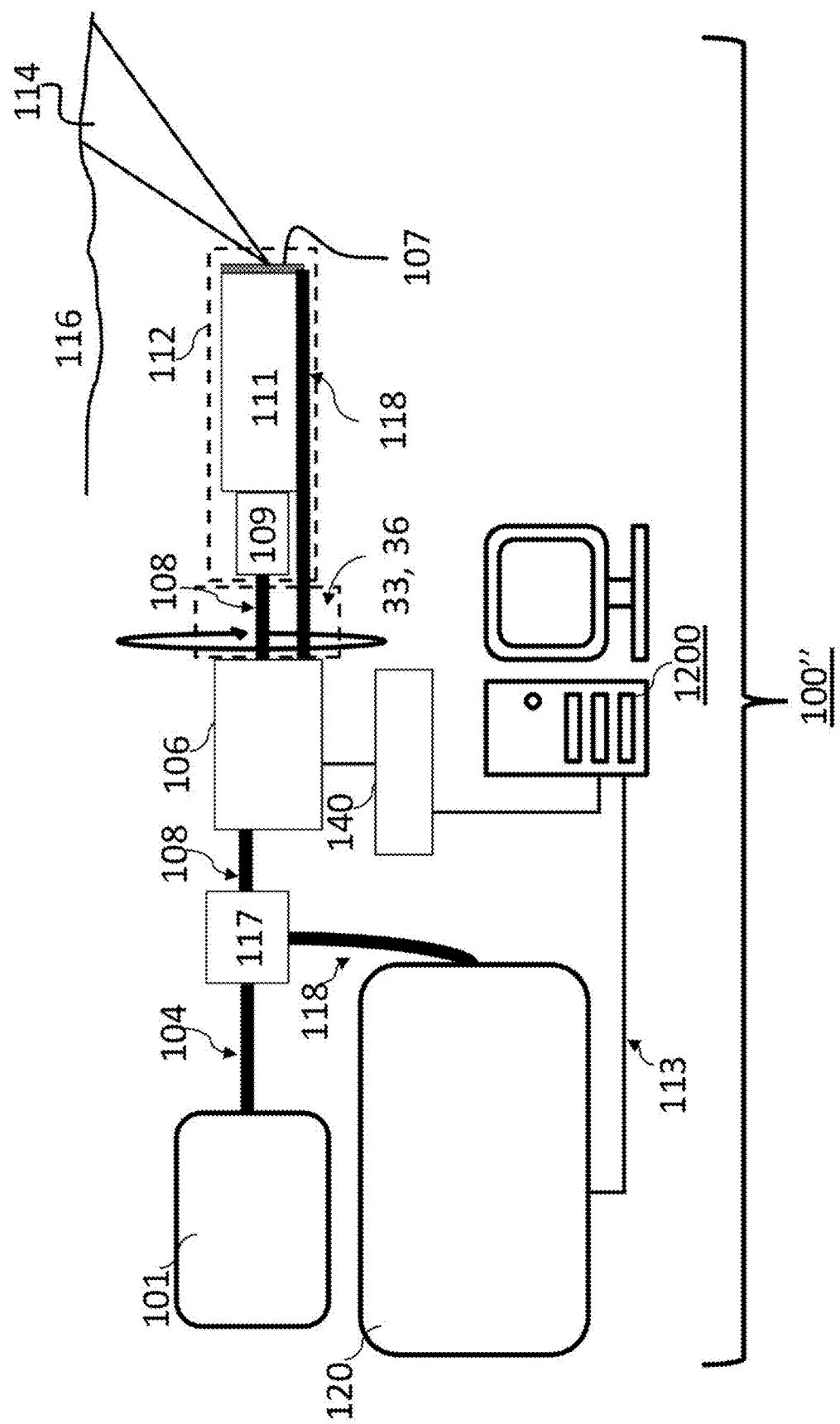

Additional embodiment examples that may use the extender and/or repeater features discussed herein are discussed generally in FIGS. 14-18 below. For example, FIG. 14 shows a ("SEE") system 100 (also referred to herein as "system 100" or "the system 100") which operates to utilize a SEE technique with an extender and/or a repeater for optical probe applications in accordance with one or more aspects of the present disclosure. As shown in FIG. 14, light emitted by a white light source 101 is transmitted by at least one illumination light transmission fiber 104 and/or 108 and is incident on a probe portion 112 (also referred to herein as "probe section 112" or "the probe 112") via a rotary junction (hereinafter, RJ) 106 (e.g., the at least one fiber(s) 104 and/or 108 may extend through the RJ 106 and into the probe portion 112). Additionally or alternatively, the light emitted by the white light source 101 may be transmitted by the at least one illumination light transmission fiber 104, 108 and is incident on the probe 112 via a deflecting or deflected section 117 and via the RJ 106 as shown in FIG. 14, for example. In one or more embodiments (see e.g., FIGS. 14 and 15B) a length of an optical fiber 108 (e.g., a first stationary fiber) may extend from the deflecting or deflected section 117 and connect to one side of the RJ 106, and a length of a different optical fiber 108 (e.g., that operates to receive light that is coupled from the RJ 106 to the different optical fiber 108 and that operates to rotate along with the at least one extender 33 and/or repeater 36, the probe 112, etc.) may extend from the other side of the RJ 106 through the at least one extender 33 and/or repeater 36 to the probe 112. In one or more embodiments of the probe 112, the white light beam is incident on a spacer 111 via a gradient-index lens (hereinafter, GRIN lens) 109. A diffraction grating (hereinafter, diffractive element) 107 is provided at the leading end portion of the spacer 111 (e.g., the GRIN lens 109 and the diffraction grating 107 are located on opposite sides of the spacer 111), and as the white light beam is incident on this diffractive element 107, a spectral sequence 114 is formed on a target (e.g., an object, a specimen, a subject, a patient, etc.) 116. In one or more embodiments, the probe 112 may not include the spacer 111, and the GRIN lens 109 may be connected to the diffractive element 107 to permit the spectral sequence 114 to be formed on the target 116. Reflected light from the spectral sequence 114 (e.g., light from the spectral sequence 114 that is formed on, and is reflected by, the target 116; light that is reflected by the target 116; etc.) is taken in by a detection fiber or cable 118. Although one detection fiber 118 is illustrated in FIGS. 14-15B, a plurality of detection fibers may be used. In one or more embodiments, the detection fiber 118 may extend to and/or near the end of the probe 112 (e.g., at the distal end 115 of the probe 112). For example, in the system 100 of FIG. 14, in the system 100' of FIG. 15A and in the system 100" of FIG. 15B, the detection fiber 118 may have a detection fiber portion (see fiber 118 extending through the probe 112 in each of FIGS. 14-15B) that extends from or through the RJ 106 through, and to and/or near (e.g., adjacent to the end 115 of the probe 112, about the end 115 of the probe 112, near the end 115 of the probe 112 closest to the target 116, etc.) the end of, the probe 112. The light taken in by the detection fiber 118 is separated into spectral components and detected by at least one detector, such as, but not limited to, a spectrometer 120 (and/or one or more components thereof as discussed herein), provided at the exit side of the detection fiber 118. In one or more embodiments, the end of the detection fiber 118 that takes in the reflected light may be disposed on or located near at least one of: the diffraction grating 107, the end of the spacer in, the end 115 of the probe 112, etc. Additionally or alternatively, the reflected light may be passed at least one of: through the probe 112, through the GRIN lens 109, through the rotary junction 106, etc., and the reflected light may be passed, via a deflecting or deflected section 117 (discussed below), to the spectrometer 120. As shown in FIGS. 14-15B, as the portion extending from the RJ 106 to the probe 112 is rotated about the rotational axis extending in the longitudinal direction of the probe 112, the spectral sequence 114 moves in a direction orthogonal to the spectral sequence 114, and reflectance information in two-dimensional directions may be obtained. Arraying these pieces (e.g., the reflectance information in two-dimensional directions) of information makes it possible to obtain a two-dimensional image.

Preferably, in one or more embodiments including the deflecting or deflected section 117 (best seen in FIGS. 14 and 15B), the deflected section 117 operates to deflect the light from the light source 101 to the probe 112, and then send light received from the probe 112 towards at least one detector (e.g., the spectrometer 120, one or more components of the spectrometer, another type of detector, etc.). In one or more embodiments, the deflected section (e.g., the deflected section 117 of the system 100 as shown in FIG. 14 and of the system 100" as shown in FIG. 15B) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100, the system 100' or of the system 100" (or any other system discussed herein, including, but not limited to, the system 30, the system 30', the system 30", the system 30''', the system 30'''', the system 30''''', the system 30'''''', the system 30''''''', the system 30'''''''', the system 1000, etc.) such as, but not limited to, one or more of the light source 101, the deflected section 117, the rotary junction 106, and/or the probe 112 (and/or one or more components thereof).

While not limited to such arrangements, configurations, devices or systems, one or more embodiments of the methods discussed herein may be used with a SEE probe as aforementioned, such as, but not limited to, for example, the system 100 (see FIG. 14), the system 100' (see FIG. 15A), the system 100" (see FIG. 15B), etc. In one or more embodiments, one user may perform the method(s) discussed herein. In one or more embodiments, one or more users may perform the method(s) discussed herein.

Figure 16:
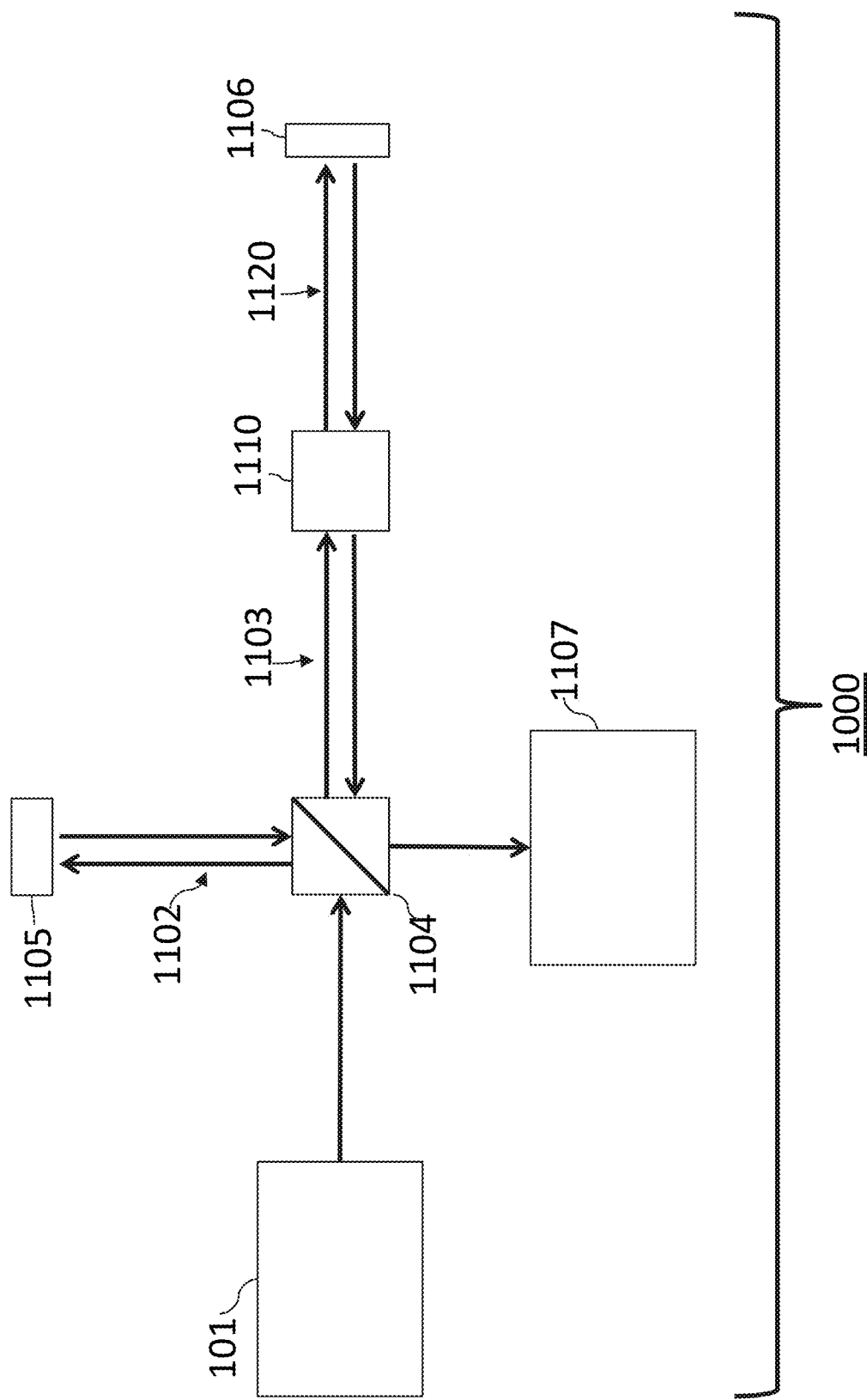
FIG. 16 a diagram showing an embodiment of an OCT system that may be used with one or more features of the present disclosure.

The devices and/or systems, such as the system 100, the system 100', the system 100", (or any other system discussed herein, including, but not limited to, the system 30, the system 30', the system 30", the system 30''', the system 30'''', the system 30''''', the system 30'''''', the system 30''''''', the system 30'''''''', the system 1000, etc.), etc., may include or be connected to a broadband light source 101 (best shown in FIGS. 14-16 for the systems 100, 100', 100", and 1000). The broadband light source 101 may include a plurality of light sources or may be a single light source. The broadband light source 101 may include one or more of a laser, an organic light emitting diode (OLED), a light emitting diode (LED), a halogen lamp, an incandescent lamp, supercontinuum light source pumped by a laser, and/or a fluorescent lamp. The broadband light source 101 may be any light source that provides light which may then be dispersed to provide light which is then used to for spectral encoding of spatial information. The broadband light source 101 may be fiber coupled or may be free space coupled to the other components of the apparatus and/or system 100 or any other embodiment (including, but not limited to, system 101' (see FIG. 15A), the system 100" (see FIG. 15B), or any other system discussed herein, including, but not limited to, the system 30, the system 30', the system 30", the system 30''', the system 30'''', the system 30''''', the system 30'''''', the system 30''''''', the system 30'''''''', the system 1000, etc., etc.) discussed herein.

As best seen in FIGS. 14-15B, the system 100, 100' and/or 100" (or any other apparatus or system discussed herein) may include a rotary junction 106 (see e.g., the systems discussed herein, including, but not limited to, the system 30, the system 30', the system 30", the system 30''', the system 30'''', the system 30''''', the system 30'''''', the system 30''''''', the system 30'''''''', the system 1000, etc.). The connection between the light source 101 and the rotary junction 106 may be a free space coupling or a fiber coupling via fiber 104. The rotary junction 106 may supply just illumination light via the rotary coupling or may supply one or more of illumination light, power, and/or sensory signal lines.

As best seen in FIGS. 14-15B, the rotary junction 106 couples the light to a first waveguide 108. In at least one embodiment, the first waveguide 108 is a single mode fiber, a multimode fiber, or a polarization maintaining fiber.

The first waveguide 108 is coupled to an optical apparatus and/or system that operates as an imager or imaging device, such as, for example the probe 112 (also referred to herein as an imager, imaging device or system, and/or optical apparatus and/or system). The optical apparatus and/or system (or the imager), or the probe, 112 may include one or more optical components, that refract, reflect, and disperse the light from the first waveguide 108 to form at least one line of illumination light 114 (e.g., additionally or alternatively, in one or more embodiments, an imaging device or probe 112 in an apparatus or system (e.g., a SEE system, an OCT system, etc.) may form a plurality of illumination lines, such as, but not limited to, from three (3) wavelength ranges in a spectrum (such as, but not limited to, in the following colors: Red (R), Green (G), Blue (B), etc.), and may overlap the plurality of illumination lines (e.g., the three (3) illumination lines) in the same or substantially the same position on the target, the object, the sample or the patient 116) on a sample, an object or a patient 116 (e.g., a predetermined area in the patient, a predetermined area in and/or on a target, through the patient, through the target, etc.). In an embodiment, the line of illumination light 114 is a line connecting focal points for a wavelength range as the illumination light exits the optical apparatus and/or system (or the imager, the imaging device, or the probe) 112, the wavelength range being determined by the light source 101. In another embodiment, the spectrometer 120 may further limit the wavelength range by only using information from specified wavelengths of interest. In another embodiment, the line of illumination light 114 is a line formed by the illumination light as the illumination light intersects a surface of the target, the sample, the object or the patient 116 for the range of wavelengths that are detected by the spectrometer 120. In another embodiment, the line of illumination light 114 is a line of illumination light in a wavelength range formed on a specific image plane which is determined by the detection optics. In one or more embodiments, only some of the points on the image line may be in focus while other points on the image line may not be in focus. The line of illumination light 114 may be straight or curved.

In an alternative embodiment, the optical apparatus and/or system (or the imager or imaging device) 112 may partially collimate the light from the waveguide 108 such that the light is focused onto the sample, the object or the patient 116 but the light is substantially collimated at a dispersive optical element such as a grating.

The apparatus (such as the system, 100, 100', 100", etc.) may include a detection waveguide 118. The detection waveguide 118 may be a multimode fiber, a plurality of multimode fibers, a fiber bundle, a fiber taper, or some other waveguide. In one or more embodiments, preferably the detection waveguide 118 comprises a plurality of detection fibers (e.g., forty-five (45) fibers, sixty (60) fibers, in a range of 45-60 fibers, less than 45 fibers, more than 60 fibers, etc.). The plurality of detection fibers of the detection waveguide 118 may be spaced apart and located around the periphery (e.g., inside the periphery, around a border of the periphery, etc.) of the imaging device or the probe 112. The detection waveguide 118 gathers light from the target, the sample, the object and/or the patient 116 which has been illuminated by light from the optical apparatus and/or system (or the imager or the imaging device, or the probe) 112. The light gathered by the detection waveguide 118 may be reflected light, scattered light, and/or fluorescent light. In one embodiment, the detection waveguide 118 may be placed before or after a dispersive element of the optical apparatus and/or system, or the probe, 112. In one embodiment, the detection waveguide 118 may be covered by the dispersive element of the optical apparatus and/or system, or the probe, 112, in which case the dispersive element may act as wavelength-angular filter. In another embodiment, the detection waveguide 118 is not covered by the dispersive element of the optical apparatus and/or system, imager or imaging device 112. The detection waveguide 118 guides detection light from the target, the sample, the object and/or the patient 116 to the spectrometer 120.

The spectrometer 120 may include one or more optical components that disperse light and guide the detection light from the detection waveguide 118 to one or more detectors. The one or more detectors may be a linear array, a charge-coupled device (CCD), a plurality of photodiodes or some other method of converting the light into an electrical signal. The spectrometer 120 may include one or more dispersive components such as prisms, a prisms, gratings, or grisms. The spectrometer 120 may include optics and opto-electronic components which allow the spectrometer 120 to measure the intensity and wavelength of the detection light from the target, the sample, the object and/or the patient 116. The spectrometer 120 may include an analog to digital converter (ADC). The separated illumination lights (e.g., illumination light 114) are emitted from a surface of the diffraction grating 107 to illuminate the object, and reflected lights (returned lights) from the object pass through the diffraction grating 107 again and are delivered to the spectrometer 120 by the detection fiber (DF) 118. In some embodiments, the reflected lights (returned lights) from the object (e.g., the object 116) are delivered to the spectrometer 120 by the detection fiber (DF) 118 without first passing through the diffraction grating 107.

The spectrometer 120 may transmit the digital or analog signals to a processor or a computer such as, but not limited to, an image processor, a processor or computer 1200, 1200' (see e.g., FIGS. 14-15B and 17-18), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the spectrometer 120. The image processor may include one or more of a CPU, DSP, FPGA, ASIC, or some other processing circuitry. The image processor may include memory for storing image, data, and instructions. The image processor may generate one or more images based on the information provided by the spectrometer 120. A computer or processor discussed herein, such as, but not limited to, the system 2, the computer 1200, the computer 1200', the image processor, may also include one or more components further discussed herein below (see e.g., FIGS. 17-18).

One or more components of the apparatus and/or system (such as the system 10, 100', 100", etc.) may be rotated via the rotary junction 106, or oscillated so as to scan a line of illumination light 114 so as to create a 2D array of illumination light. A 2D image may be formed by scanning a spectrally encoded line from the optical apparatus and/or system, the imager or imaging device, or the probe, 112 across the target, the sample, the object and/or the patient 116. The apparatus and/or system (such as the system 100, 100', 100", etc.) may include an additional rotary junction that couples the light from the detection fiber 118 to the spectrometer 120. Alternatively, the spectrometer 120 or a portion of the spectrometer 120 may rotate with the fiber 118. In an alternative embodiment, there is no rotary junction 106 and the light source rotates with the fiber 108. An alternative embodiment may include an optical component (mirror) after a dispersive element in the optical system or imager, or the probe, 112 which rotates or scans the spectrally encoded line of illumination light across the target, the sample, the object and/or the patient 116 substantially perpendicular to the spectrally encoded line of illumination light 114 in a linear line to produce a 2D image or circumferentially in a circle so as to produce a toroidal image. Substantially, in the context of one or more embodiments of the present disclosure, means within the alignment and/or detection tolerances of the apparatus and/or system (such as the system 100, 100', 100", 1000, or any other system discussed herein, including, but not limited to, the system 30, the system 30', the system 30", the system 30''', the system 30'''', the system 30''''', the system 30'''''', the system 30''''''', the system 30'''''''', the system 1000, etc.) and/or any other system being discussed herein may be utilized or accounted for. In an alternative embodiment, there is no rotary junction 106 and an illumination end of the optical apparatus and/or system or the imager, or the probe, 112 is scanned or oscillated in a direction perpendicular to the illumination line. The at least one extender 33 and/or the at least one repeater 36 may be positioned between the RJ 106 and the probe 112 as shown diagrammatically in at least FIGS. 14-15B.

In one or more alternative embodiments, a dispersive element 107 (i.e., a diffraction grating) may be used in the optical apparatus and/or system, or the probe, 112 as shown, respectively, in FIGS. 14-15B. In one or more embodiments (best seen in FIGS. 14-15B), light that has been emitted from the core of the end portion of the illumination optical fiber or the first waveguide 108 may enter a spacer 111 via a refractive-index distribution lens (hereinafter referred to as "gradient index (GRIN) lens") 109. The diffraction grating 107 is formed at the tip portion of the spacer 111 as shown in FIGS. 14-15B, and a spectral sequence 114 is formed on the target, the subject, object or sample 116 by a light flux (e.g., of white light) entering the diffraction grating 107. FIGS. 14 and 15B illustrate alternative embodiments of respective apparatuses and/or systems 100, 100" including a spectrometer as shown in FIG. 15A (see e.g., system 100'), with the exception being that a deflecting or deflected section 117 is incorporated into the system 100 of FIG. 14 and into the system 100" of FIG. 15B such that the cable or fiber 104 and/or the cable or fiber 108 connecting the light source 101 to the rotary junction 106 and/or the optical apparatus and/or system (or the probe) 112 and the cable or fiber 118 connecting the spectrometer 120 to the rotary junction 106 and/or the optical apparatus and/or system or imager (or the probe) 112 pass through, and are connected via, the deflected section 117 (discussed further below).

In at least one embodiment, a console or computer 1200, 1200' operates to control motions of the RJ 106 via a Motion Control Unit (MCU) or a motor 140, acquires intensity data from the detector(s) in the spectrometer 120, and displays the scanned image (e.g., on a monitor or screen such as a display, screen or monitor 1209 as shown in the console or computer 1200 of any of FIGS. 14-15B and FIG. 17 and/or the console 1200' of FIG. 18 as further discussed below). In one or more embodiments, the MCU or the motor 140 operates to change a speed of a motor of the RJ 106 and/or of the RJ 106. The motor may be a stepping or a DC servo motor to control the speed and increase position accuracy. In one or more embodiments, the deflection or deflected section 117 may be at least one of: a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc. In one or more other embodiments, the rotary junction 106 may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 108 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 118, the spectrometer 120, the computer 1200, the computer 1200', etc. The detection fibers, such as the detection fiber(s) 118, may surround the illumination fiber, such as the IF 108, and the detection fibers may or may not be covered by the grating, such as the grating 107.

In an embodiment, the first waveguide 108 may be single mode fiber. In an alternative embodiment, the first waveguide 108 may be a multimode fiber or a double clad fiber. In an embodiment, the second waveguide 118 may be a multi-mode fiber a single mode fiber, or a fiber bundle.

In an alternative embodiment, the first waveguide 108 may be an inner core of a double-clad fiber, while the second waveguide 118 may be between the inner core and the outer cladding of the double clad fiber. If a double clad fiber is used, an alternative embodiment may include an optical coupler for guiding illumination light to the inner core, and the optical coupler may also receive detection light from the outer waveguide which is then guided to the spectrometer 120.

In one or more embodiments, a SEE probe may include the illumination fiber(s) 104 and/or 108, the diffraction grating 107 and the detection fiber 118, and the illumination fiber(s) 104 and/or 108, the diffraction grating 107 and the detection fiber 118 may be housed by a metal or plastic tube to enhance the SEE probe's robustness for rotational motions and external stress by insertion. The SEE probe may further include a lens at the distal end of the probe, which may be located after the diffraction grating 107 (not shown), or between the diffraction grating 107 and the illumination fiber 108 (see e.g., the lens or prism 109 as shown in FIGS. 14-15B and as discussed further below), or between the diffraction grating 107 and the detection fiber 118. In one or more embodiments, a SEE probe is incorporated with the motor or MCU 140 at a proximal side, which enables the SEE probe to scan in a horizontal direction, for example, with a periodical arc motion. In one or more embodiments, the motor 140 may be a rotational motor to achieve, for example, circumferential viewing. In some embodiments, the systems 100, 100', 100", or any other system discussed herein, may include one or more rotary junctions (not shown) that are configured to rotate the illumination fiber 108 or the illumination fiber 108 and the detection fiber 118. In at least one embodiment, the detection fiber 118 may be coupled with the spectrometer 120 including a diffraction grating and the at least one detector of the spectrometer 120.

The output of the one or more components of any of the systems discussed herein may be acquired with the at least one detector and/or the spectrometer 120, e.g., such as, but not limited to, photodiodes, Photomultiplier tube(s) (PMTs), line scan camera(s), or multi-array camera(s). Electrical analog signals obtained from the output of the system 100 and/or the spectrometer thereof are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector and/or the spectrometer 120 comprises three detectors configured to detect three different bands of light. In yet other embodiments, the spectrometer 120 is configured to generate three 2D images from three different bands of light (e.g., red, green, and blue) where these three 2D images may be combined to form a single image having color information. In yet other embodiments, multiple spectrometers 120 may be used to generate different 2D images from the three different bands of light.

In accordance with at least one aspect of the present disclosure and as aforementioned, one or more methods for performing tissue characterization when using a SEE system are provided herein. At least one embodiment of a method for characterizing tissue using a SEE system may include one or more of the following: (i) setting object information; (ii) designating one or more imaging conditions; (iii) start imaging; (iv) coordinating intensities to construct a SEE image; (v) determining tissue type; (vi) displaying tissue type on a center (or other predetermined location) of a scanned tissue image; and (vii) determining whether to change a region of interest (ROI); (viii) if "Yes" the prior step, then adjusting a measuring position toward the center of the image and then determining whether to end the exam; if "No", repeating the prior step, and if "Yes", end the process), or if "No" in the prior step of determining whether to change the ROI, then keep displaying the scanned tissue image and tissue type and then repeat the step of determining whether to change the ROI.

In some embodiments, the deflecting section 117 operates to deflect the light from the light source 101 to the SEE probe, and then send light received from the SEE probe towards the at least one detector and/or the spectrometer 120. In one or more embodiments, the deflecting section 117 may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc.

In one or more embodiments, a SEE probe may be connected to one or more systems (e.g., the system 100, the system 100', the system 100", the system 1000, or any other system discussed herein, including, but not limited to, the system 30, the system 30', the system 30", the system 30''', the system 30"", the system 30""", the system 30"""", the system 30""""", the system 30"""""", the system 1000, etc.) with a connection member or interface module. For example, when the connection member or interface module is a rotary junction for either a SEE probe or the aforementioned OCT system, the rotary junction may be at least one of: a contact rotary junction, a lenseless rotary junction, a lens-based rotary junction, or other rotary junction known to those skilled in the art. The rotary junction may be a one channel rotary junction or a two channel rotary junction.

In one or more embodiments, a SEE probe may further include a lens located between the DG 107 and the sample or object (e.g., object 116). Preferably, in such an embodiment, the lens receives light from the fiber 108, DG 107 and/or the prism 109 (depending on which system, such as the system 100, the system 100', the system 100", etc., includes the lens) and passes the light therethrough towards the sample. After illuminating the sample, the light passes through the lens back towards the DG 107 and/or the prism 109 and into the fiber 118, and/or directly into the fiber 118. In one or more embodiments, the lens may or may not be tilted or angled.

Unless otherwise discussed herein, like numerals indicate like elements. For example, while variations or differences exist between the systems, such as, but not limited to, the system 100, the system 100' and the system 100", the system moo, or any other system discussed herein, including, but not limited to, the system 30, the system 30', the system 30", the system 30''', the system 30"", the system 30""", the system 30"""", the system 30""""", the system 30"""""", the system 1000, etc., one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 140, the at least one detector and/or the spectrometer 120, and/or one or more other elements of the system 100, may operate in the same or similar fashion to those like-numbered elements of one or more other systems, such as, but not limited to, the system 100', the system 100", the system 1000, or any other system discussed herein, including, but not limited to, the system 30, the system 30', the system 30", the system 30''', the system 30"", the system 30""", the system 30"""", the system 30""""", the system 1000, etc. as discussed herein. Those skilled in the art will appreciate that alternative embodiments of the system 100, the system 100', the system 100", the system 100, any other system discussed herein, including, but not limited to, the system 30, the system 30', the system 30", the system 30''', the system 30"", the system 30""", the system 30"""", the system 30""""", the system 30"""""", the system 1000, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 100', and the system 100", for example, as discussed herein, there are similarities. Likewise, while the console or computer 1200 may be used in one or more systems (e.g., the system 100, the system 100', the system 100", the system moo, or any other system discussed herein, including, but not limited to, the system 30, the system 30', the system 30", the system 30''', the system 30"", the system 30""", the system 30"""", the system 30""""", the system 30"""""", the system 1000, etc.), one or more other consoles or computers, such as the console or computer 1200', may be used additionally or alternatively.

There are many ways to compute intensity, viscosity, resolution (including increasing resolution of one or more images), creation of color images or any other measurement discussed herein, digital as well as analog. In at least one embodiment, a computer, such as the console or computer 1200, 1200', may be dedicated to control and monitor the imaging (e.g., SEE, OCT, etc.) devices, systems, methods and/or storage mediums described herein.

The electric signals used for imaging may be sent to one or more processors, such as, but not limited to, a computer 1200 (see e.g., FIG. 17), a computer 1200' (see e.g., FIG. 18), etc. as discussed further below, via cable(s) or wire(s), such as, but not limited to, the cable(s) or wire(s) 113 (see FIGS. 14-15B).

In accordance with one or more aspects of the present disclosure, one or more methods for performing imaging may be performed using an extender and/or a repeater as discussed herein. Any imaging method employing at least one rotating waveguide may benefit from using the extender 33 and/or repeater 36 of the present disclosure.

The at least one extender and/or repeater features discussed herein may be applied to a SEE system as aforementioned or an optical coherent tomography (OCT) system with an optical rotary junction in one or more embodiments. This embodiment may be used for industrial purposes. FIG. 16 shows an exemplary system 1000 which can utilize an OCT technique with one or more extenders 33 and/or repeaters 36. A light from a light source 101 delivers and splits into a reference arm 1102 and a sample arm 1103 with the splitter 1104. A reference beam is reflected from a reference mirror 1105 in the reference arm 1102 while a sample beam is reflected or scattered from a sample 1106 through a PIU (patient interface unit or probe interface unit) 1110 and a catheter 1120 in the sample arm 1103. The PIU 1110 may include a rotary junction, such as the RJ 106, for rotation of the catheter 1120. In one or more embodiments, the one or more extenders 33 and/or repeaters 36 may be positioned between the RJ 106 and the sample 1106 as discussed herein. Both beams combine at the splitter 1104 and generate interference patterns. The output of the interferometer is detected with detector(s) 1107, such as, but not limited to, photodiode(s) or multi-array camera(s). The interference patterns are generated only when the path length of the sample arm 1103 matches that of the reference arm 1102 to within the coherence length of the light source 101.

Figure 17:
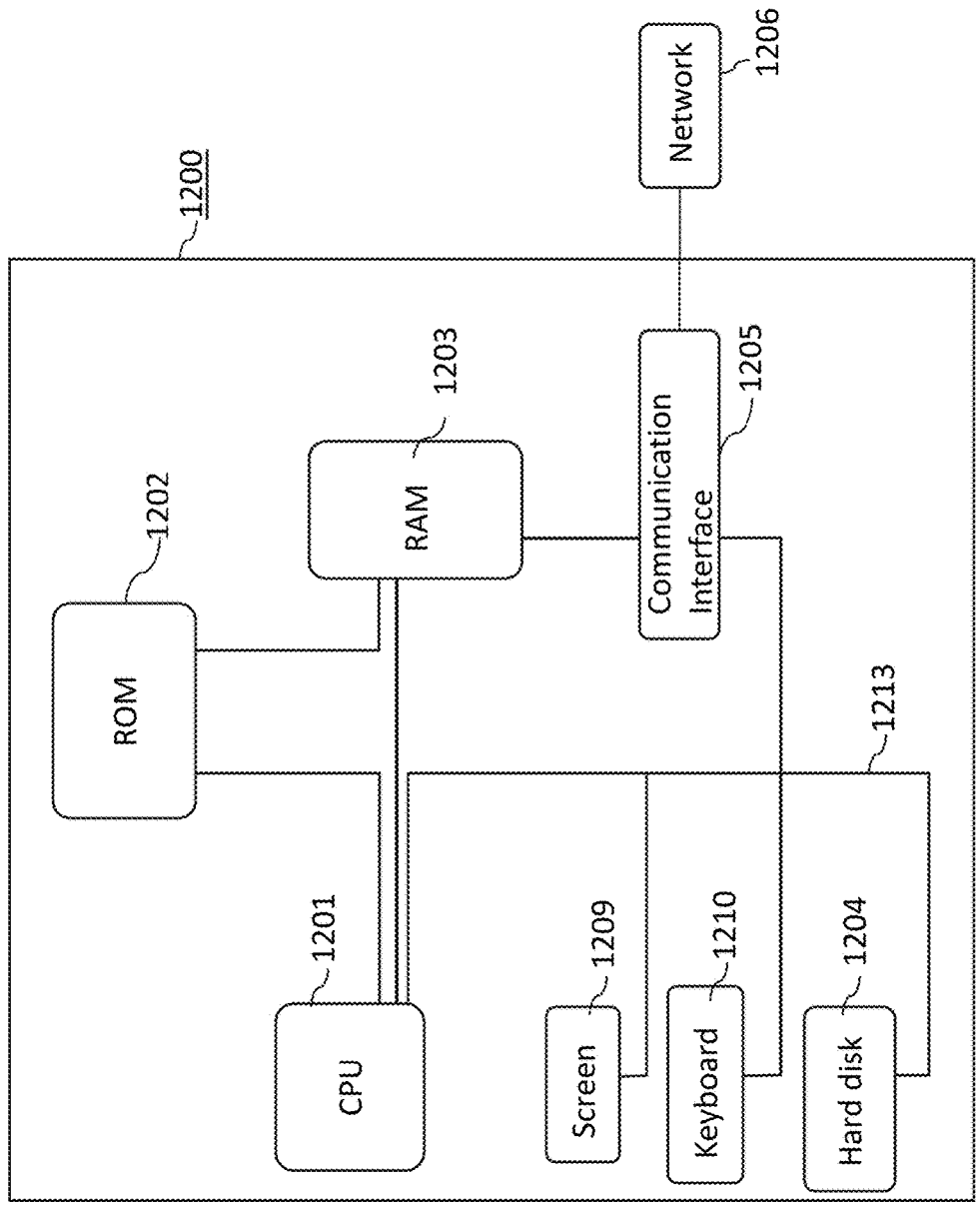
FIG. 17 shows a schematic diagram of an embodiment of a computer that may be used with one or more embodiments of an extender and/or repeater apparatus or system in accordance with one or more aspects of the present disclosure.

Various components of a computer system 1200 (see e.g., the console 2 of FIG. 13 which may be the computer 1200, 1200'; the console or computer 1200 as shown in FIGS. 14-15B) are provided in FIG. 17. A computer system 1200 (and/or the computer 2 of FIG. 13) may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., including but not limited to, being connected to the console 31, the probe 112, the extender 33, the repeater 26, any motor (such as the motor 140) discussed herein, a light source (such as the light source 101), etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, a system using at least one extender 33 and/or at least one repeater 36), and one or more other computer systems 1200 may include one or more combinations of the other aforementioned components (e.g., the one or more lines 1213 of the computer 1200 may connect to other components via line 113 and/or wirelessly). The CPU 1201 is configured to read and perform computer-executable instructions stored in a storage medium. The computer-executable instructions may include those for the performance of the methods and/or calculations described herein. The system 1200 (and/or the computer 2) may include one or more additional processors in addition to CPU 1201, and such processors, including the CPU 1201, may be used for tissue or sample characterization, diagnosis, evaluation and/or imaging. The system 1200 may further include one or more processors connected via a network connection (e.g., via network 1206). The CPU 1201 and any additional processor being used by the system 1200 (and/or the computer 2) may be located in the same telecom network or in different telecom networks (e.g., performing technique(s) discussed herein may be controlled remotely or wirelessly).

The I/O or communication interface 1205 provides communication interfaces to input and output devices, which may include the medical device 1, the guidance device 105, the PACS 4, the CT scanner 5, a light source, a spectrometer, the communication interface of the computer 1200 may connect to other components discussed herein via line 113 (as diagrammatically shown in FIG. 17), a microphone, a communication cable and a network (either wired or wireless), a keyboard 1210, a mouse (see e.g., the mouse 1211 as shown in FIG. 17), a touch screen or screen 1209, a light pen and so on. The Monitor interface or screen 1209 provides communication interfaces thereto.

Any methods and/or data of the present disclosure, such as the methods for performing tissue or sample characterization, diagnosis, examination and/or imaging (including, but not limited to, increasing image resolution), planning and/or performing a medical procedure, for example, with an extender and/or a repeater as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 18), SRAM, etc.), an optional combination thereof, a server/database, etc. may be used to cause a processor, such as, the processor or CPU 1201 of the aforementioned computer system 1200 (and/or the computer 2) to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200 (and/or of the computer 2), etc., as described above may be achieved utilizing suitable hardware, such as that illustrated in FIGS. 1A-18. Functionality of one or more aspects of the present disclosure may be achieved utilizing suitable hardware, such as that illustrated in FIG. 17. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 17 and/or FIG. 18) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

Figure 18:
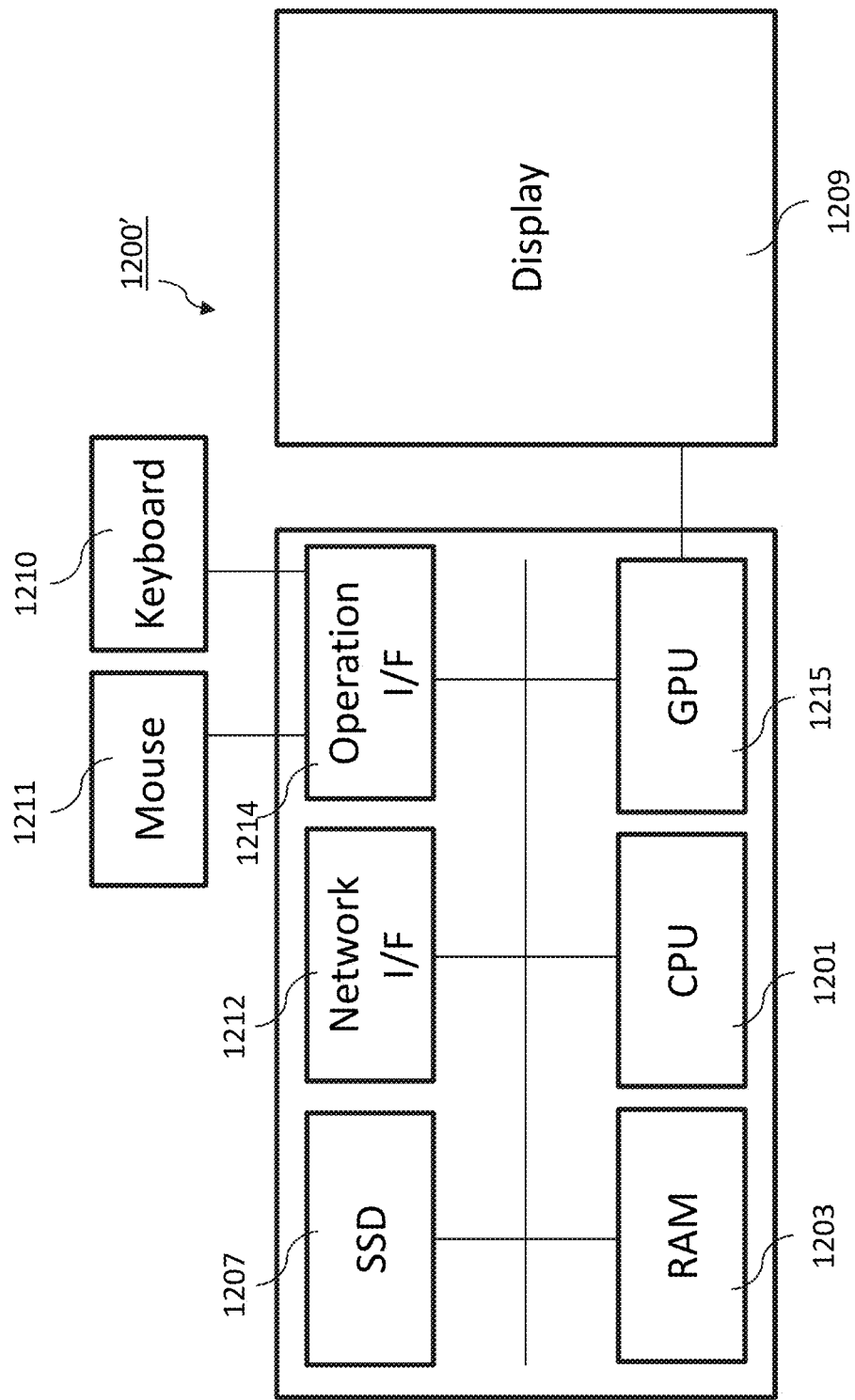
FIG. 18 shows a schematic diagram of another embodiment of a computer that may be used with one or more embodiments of an extender and/or repeater apparatus or system in accordance with one or more aspects of the present disclosure.

As aforementioned, hardware structure of an alternative embodiment of a computer or console 1200' is shown in FIG. 18. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with the medical device 1, the guidance device 105, the PACS 4, the CT scanner 5, communication devices (e.g., to discuss the procedure with peers, clinicians, etc.) via the operation interface 1214 or the network interface 1212 (e.g., via wired or wireless connection). The computer 1200' may connect with a motor, a console, an extender and/or a repeater or any other component of the device(s) or system(s) discussed herein via the operation interface 1214 or the network interface 1212 (e.g., via a cable or fiber, such as the cable or fiber 113 as similarly shown in FIGS. 14-15B). A computer, such as the computer 1200', may include a motor and/or motion control unit (MCU) in one or more embodiments. The operation interface 1214 is connected with an operation unit such as a mouse device 1211, a keyboard 1210 or a touch panel device. The computer 1200' may include two or more of each component.

In at least one embodiment, at least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

In one or more embodiments, the computer, such as the computer 2, 1200, 1200', communicates with one or more other system components (e.g., a motor or an MCU, the medical device 1, the guidance device 105, the PACS 4, the CT scanner 5 or other type of scanner, of system 10 or other device or system, or any component(s) thereof (such as, but not limited to, at least one extender 33, at least one repeater 36, etc.), being used for medical procedure (e.g., needle guidance, ablation, biopsy, visualization and manipulation of registration result(s), imaging, etc.) planning and/or performance) to perform imaging, planning and/or performance. The monitor or display 1209 displays the plan and performance and/or guidance steps (e.g., in real time), and may display other information about the imaging condition or about an object to be imaged and operated on during the procedure. The monitor 1209 also provides a graphical user interface for a user to operate an ablation planning and/or performance and/or needle guidance or ablation (or other medical procedure) probe guidance device or system (e.g., the system 10). An operation signal is input from the operation unit (e.g., such as, but not limited to, a mouse device 1211, a keyboard 1210, a touch panel device, etc.) into the operation interface 1214 in the computer 2, 1200, 1200', and corresponding to the operation signal the computer 2, 1200, 1200' instructs the system (e.g., the system 10) to set or change the imaging, planning and/or performance condition(s), and to start or end any portion of any of the method(s) discussed herein. The computer, such as the computer 2, 1200, 1200', may communicate with an MCU, an extender, a repeater, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 2, 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 7,872,759; 7,889,348; 8,045,177; 8,145,018; 8,289,522; 8,838,213; 8,928,889; 9,254,089; 9,295,391 to Tearney et al.; 9,415,550; 9,557,154 as well as the disclosures in Patent Application Publication Nos. WO2015/116951; WO2015/116939; WO2017/117203; WO2017/024145; WO2017/165511A1; in U.S. Pat. No. 9,332,942; in U.S. Patent Publication Nos. 2012/0101374; 2016/0349417; US2017/0035281; 2017/167861; 2017/0168232; 2017/0176736; 2017/0290492; 2017/0322079; and in U.S. Non-Provisional patent application Ser. No. 15/418,329 filed Jan. 27, 2017 and published as U.S. Pat. Pub. No. 2018/0017778, each of which patents, patent publications and application(s) are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, and 2016/0228097, and WO 2016/144878, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An imaging system comprising:
   a stationary portion that operates to include or be connected to at least one signal source and at least one signal detector subsystem;
   a probe having at least one rotatable signal transmitting element, a first end or a proximal end with a signal transmitting connector, and a second end or a distal end operating to communicate or interact a probing signal with, and/or cause the probing signal to interact with and return data from, a specimen, sample, or object;
   a rotary joint including at least one rotatable signal transmitting element, the rotary joint operating to transmit signals between the stationary portion of the system and the at least one rotatable signal transmitting element of the rotary joint; and an elongated extender including a rotatable signal transmitting element, at least one rotational drive that is spaced away from the rotary joint and that operates to be rotationally driven or powered such that the at least one rotational drive imparts or adds rotational movement, and a signal transmitting connector, the elongated extender operating to transmit a signal between the at least one rotatable signal transmitting element of the rotary joint at a first end of the elongated extender and the signal transmitting connector of the probe at a second end of the elongated extender via the signal transmitting connector of the elongated extender, at least one of the at least one rotational drive being disposed at or near the second end of, and in proximity or adjacent to the signal transmitting connector of, the elongated extender that is attached to the probe such that the at least one of the at least one rotational drive is closer to the probe than the rotary joint.

2. The system of claim 1, wherein one or more of the following:
  (a) the at least one rotatable signal transmitting element of the elongated extender, the rotary joint, and the probe is comprised of rotatable optical fiber;
  (b) the elongated extender is configured and operates to one or more of: (i) maintain rotational synchronization, or substantial rotational synchronization, between the first and second ends of the elongated extender, and (ii) avoid or reduce Non-Uniform Rotational Distortion on or in an image of the specimen, sample, or object obtained by the imaging system;
  (c) the elongated extender is further configured to impart rotational motion on the at least one rotatable signal transmitting element of the rotary joint and on the signal transmitting connector of the probe;
  (d) one or more of the rotary joint and the elongated extender further operate to impart rotational motion on at least the probe; and/or
  (e) the extender has a fixed length and/or a fixed size and/or shape.

3. The system of claim 2, wherein one or more of the following:
  (i) the elongated extender further comprises a hollow rotatable drive shaft disposed or arranged to include or contain the rotatable optical fiber and operating to transmit and distribute torque along the at least one rotatable signal transmitting element between the first end and the second end of the elongated extender; and/or
  (ii) the elongated extender further comprises a hollow rotatable drive shaft disposed or arranged to include or contain the rotatable signal transmitting element of the elongated extender and operating to transmit and distribute torque along the rotatable signal transmitting element of the elongated extender between the first end and the second end of the elongated extender.

4. The system of claim 3, wherein the at least one rotational drive of the elongated extender is rotationally synchronized with rotational motion of the rotary joint and disposed along a length of the rotatable optical fiber of the elongated extender, the at least one rotational drive operating to impart the rotational motion on the signal transmitting connector of the elongated extender.

5. The system of claim 3, wherein the elongated extender further comprises one or more of the following:

(i) a non-rotatable sheath disposed around the rotatable drive shaft and the drive shaft operates to flex at at least one portion of the drive shaft;
  (ii) the at least one rotational drive comprises a plurality of rotationally synchronized rotational drives disposed along the length of the drive shaft, and each rotational drive of the plurality of rotational drives operates to impart a rotational motion on the drive shaft;
  (iii) the rotatable drive shaft of the elongated extender further operates to transmit axial motion; and/or
  (iv) a motor that operates to provide the rotational drive or power for the at least one rotational drive or a motor that operates to provide the rotational drive or power for the at least one rotational drive and that allows an optical fiber to pass through the motor on or substantially on an axis of rotation.

6. The system of claim 5, wherein one or more of the following:
  at least one rotational drive of the elongated extender is fitted with at least one spline-like nut, and a portion of the rotatable drive shaft proximal, near or adjacent to the at least one rotational drive includes a matching cross-section that operates to slide in an axial direction and to transmit torque in a rotational direction; and/or
  the at least one rotational drive of the elongated extender comprises more than one rotationally synchronized rotational drive disposed along the length of the drive shaft, each rotationally synchronized rotational drive being fitted with at least one spline-like nut; and portions of the rotatable drive shaft proximal, near or adjacent to each rotational drive include a matching cross-section that operates to slide in an axial direction and to transmit torque in a rotational direction.

7. The system of claim 6, wherein the portion of the rotatable drive shaft proximal, near or adjacent to the at least one rotational drive is a low-flexing or substantially rigid tube of approximately oval cross-section rigidly attached to the signal transmitting connector of the elongated extender.

8. The system of claim 7, wherein the low-flexing or substantially rigid tube of the elongated extender has an axially sliding support disposed in proximity to, or adjacent or close to, the signal transmitting connector of the elongated extender, the axially sliding support operating to allow the low-flexing or substantially rigid tube to spin freely and to restrict or prevent one or more cross-axis displacements.

9. The system of claim 1, wherein one or more of the following:
  the at least one rotational drive is disposed proximal to the signal transmitting connector of the probe to reduce or eliminate image Non-Uniform Rotational Distortion (NURD);
  the at least one of the at least one rotational drive is located in a distal portion of the elongated extender; and/or
  the one rotational drive is operated or used without using a motor for the rotary joint.

10. The system of claim 6, wherein a portion of the rotatable drive shaft of the elongated extender is fitted with a lead screw, and the elongated extender further comprises a non-rotatable matching lead screw nut disposed along a length of the lead screw operating to impart axial motion to the rotatable drive shaft from the drive shaft rotation.

11. The system of claim 10, wherein the non-rotatable matching lead screw nut operates to control engagement and disengagement from the lead screw portion of the rotatable drive shaft.

12. The system of claim 6, wherein the rotatable elongated extender further comprises a linear slide operating to allow for axial movement of the at least one rotational drive and/or the rotatable drive shaft of the elongated extender along an axis of rotation.

13. The system of claim 12, wherein the linear slide of the elongated extender further comprises a drive.

14. The system of claim 2, wherein the at least one rotational drive of the elongated extender is:
   (i) rotationally synchronized with rotational motion of the rotary joint;
   (ii) disposed along a length of the rotatable optical fiber; and
   (iii) operating to impart rotational motion on the signal transmitting connector of the elongated extender.

15. The system of claim 14, wherein the elongated extender further comprises a non-rotatable sheath disposed around the rotatable optical fiber.

16. The system of claim 2, wherein one or more of the following:
   (i) the elongated extender further comprises a non-rotatable sheath disposed around the rotatable drive shaft; and/or
   (ii) the rotatable drive shaft of the elongated extender further operates to transmit axial motion.

17. The system of claim 1, wherein one or more of the following:
   (i) the stationary portion includes the at least one signal source and the at least one signal detector subsystem;
   (ii) the at least one signal source comprises at least one light or broadband laser source;
   (iii) the stationary portion further includes an interference optical system that operates to: (a) receive and divide light from the at least one light or broadband laser source into a first light with which the specimen, object, or sample is to be irradiated and which travels along a sample arm of the interference optical system and a second reference light, (b) send the second reference light along a reference arm of the interference optical system for reflection off of a reference reflection of the interference optical system, and (c) generate interference light by causing reflected or scattered light of the first light with which the specimen, object, or sample has been irradiated and the reflected second reference light to combine or recombine, and/or to interfere, with each other, the interference light generating one or more interference patterns;
   (iv) the at least one signal detector subsystem includes one or more of the following: at least one detector that operates to acquire one or more intensities and/or the one or more interference patterns to measure the interference or the one or more interference patterns between the combined or recombined light, a spectrometer;
   (v) the stationary portion further includes a deflecting section that operates to deflect the light from the light or broadband laser source to the interference optical system, and then send light received from the interference optical system towards the at least one signal detector;
   (vi) the stationary portion further includes a deflecting section that operates to deflect the light from the light or broadband laser source to the interference optical system, and then send light received from the interference optical system towards the at least one signal detector, and the deflecting section comprises at least one of: one or more interferometers, a circulator, a beam splitter, an isolator, a coupler, a fusion fiber coupler, a partially severed mirror with holes therein, and a partially severed mirror with a tap;
   (vii) the system further includes at least one processor that operates to process a signal from the at least one detector to acquire information of the specimen, object, or sample;
   (viii) the system further includes a motor that operates to rotate one or more of the following: the at least one rotatable signal transmitting element of the rotary joint, the extender, and the rotatable probe; and/or
   (ix) the system operates with, connected to or as a part of a Spectrally Encoded Endoscopy ("SEE") apparatus or system, an Optical Coherence Tomography ("OCT") apparatus or system, and/or a medical device.

18. The system of claim 17, further comprising one or more of the following:
   (i) a probe interface unit spaced away from, and disposed outside of, the stationary portion and/or disposed near the specimen, sample, or object; and/or
   (ii) a display or screen that operates to display a user interface via which an operator or user of the system selects one or more positions, one or more lines or one or more regions of interest from which to obtain the one or more intensities and/or the one or more interference patterns.

19. An imaging system comprising:
   a stationary portion that operates to include or be connected to at least one signal source and at least one signal detector subsystem;
   a rotary joint including at least one rotatable signal transmitting element, the rotary joint operating to transmit signals between the stationary portion of the system and the at least one rotatable signal transmitting element of the rotary joint;
   an elongated probe having at least one rotatable signal transmitting element, a proximal end or a first end with a signal transmitting connector operating to mate with the at least one rotatable signal transmitting element of the rotary joint, a distal end or a second end operating to communicate or interact a probing signal with, and/or cause the probing signal to interact with and return data from, a specimen, sample, or object, and at least one coupling region operating to transmit rotational motion from an external drive to the at least one rotatable signal transmitting element of the elongated probe; and
   at least one rotational drive rotationally synchronized, or substantially rotationally synchronized, with rotational motion of the rotary joint, the at least one rotational drive operating to be disposed along the length of the at least one coupling region and operating to impart rotational motion on the at least one rotatable signal transmitting element of the probe.

20. An imaging system comprising:
   a stationary portion that operates to connect to, and receive light from, a light or broadband laser source and transmit light to a detector;
   a rotatable probe in optical communication with the stationary portion;
   a rotary joint operating to transmit rotational motion to the rotatable probe; and
   at least one extender located between the rotary joint and the rotatable probe, the at least one extender including at least one rotational drive that is spaced away from the rotary joint and that operates to be rotationally driven or powered such that the at least one rotational drive imparts or adds rotational movement, at least one of the at least one rotational drive being disposed closer to the rotatable probe than the rotary joint, the at least one extender operating to rotate, the rotation of the at least one extender being substantially synchronized or synchronized with a rotation of the rotary joint, and/or the at least one extender operating to avoid or reduce Non-Uniform Rotational Distortion on an image obtained by the imaging system.

21. An imaging system comprising:
a stationary portion that operates to include or be connected to at least one signal source and at least one signal detector subsystem;
a probe having at least one rotatable signal transmitting element, a first end or a proximal end with a signal transmitting connector, and a second end or a distal end operating to communicate or interact a probing signal with, and/or cause the probing signal to interact with and return data from, a specimen, sample, or object;
a rotary joint including at least one rotatable signal transmitting element, the rotary joint operating to transmit signals between the stationary portion of the system and the at least one rotatable signal transmitting element of the rotary joint; and
an elongated extender including a rotatable signal transmitting element, at least one rotational drive, and a signal transmitting connector, the elongated extender operating to transmit a signal between the at least one rotatable signal transmitting element of the rotary joint at a first end of the elongated extender and the signal transmitting connector of the probe at a second end of the elongated extender via the signal transmitting connector of the elongated extender,
wherein one or more of the rotary joint and the elongated extender further operate to impart rotational motion on at least the probe.

22. The system of claim 21, wherein one or more of the following:
the at least one rotational drive is disposed proximal to the signal transmitting connector of the probe to reduce image Non-Uniform Rotational Distortion (NURD);
the at least one rotational drive comprises one drive located in the distal portion of the elongated extender; and/or
the one drive is operated or used without using a motor for the rotary joint.

23. The system of claim 21, wherein one or more of the following:
(a) the at least one rotatable signal transmitting elements of the elongated extender, the rotary joint, and the probe are comprised of rotatable optical fiber;
(b) the elongated extender is configured and operates to one or more of: (i) maintain rotational synchronization, or substantial rotational synchronization, between the first and second ends of the elongated extender, and (ii) avoid or reduce Non-Uniform Rotational Distortion on or in an image of a sample or object obtained by the imaging system;
(c) the elongated extender is further configured to impart rotational motion on the at least one rotatable signal transmitting element of the rotary joint and on the signal transmitting connector of the probe; and/or
(d) the extender has a fixed length and/or a fixed size and/or shape.

24. The system of claim 23, wherein the elongated extender further comprises one or more of the following:
(i) a hollow rotatable drive shaft disposed or arranged to include or contain the rotatable optical fiber and operating to transmit and distribute torque along the optical fiber between the first end and the second end of the elongated extender;
(ii) a hollow rotatable drive shaft disposed or arranged to include or contain the rotatable optical fiber and operating to transmit and distribute torque along the optical fiber between the first end and the second end of the elongated extender, and a non-rotatable sheath disposed around the rotatable drive shaft and the drive shaft operates to flex at at least one portion of the drive shaft;
(iii) a hollow rotatable drive shaft disposed or arranged to include or contain the rotatable optical fiber and operating to transmit and distribute torque along the optical fiber between the first end and the second end of the elongated extender, wherein the at least one rotational drive comprises a plurality of rotationally synchronized drives disposed along the length of the drive shaft, and each drive of the plurality of rotational drives operates to impart a rotational motion on the drive shaft; and/or
(iv) a hollow rotatable drive shaft disposed or arranged to include or contain the rotatable optical fiber and operating to transmit and distribute torque along the optical fiber between the first end and the second end of the elongated extender, wherein the rotatable drive shaft of the elongated extender further operates to transmit axial motion.

25. The system of claim 24, wherein one or more of the following:
(i) the at least one rotational drive of the elongated extender is fitted with at least one spline-like nut, and a portion of the rotatable drive shaft proximal, near or adjacent to the at least one rotational drive includes a matching cross-section that operates to slide in an axial direction and to transmit torque in a rotational direction; and/or
(ii) the at least one rotational drive is disposed along a length of the rotatable optical fiber of the elongated extender, the at least one rotational drive operating to impart rotational motion on the signal transmitting connector of the elongated extender.

* * * * *